_United States Patent_ [19]

Rebeiz

[11] Patent Number: 5,321,001
[45] Date of Patent: Jun. 14, 1994

[54] PHOTODYNAMIC PLANT DEFOLIANTS

[75] Inventor: Constantin A. Rebeiz, Urbana, Ill.

[73] Assignee: The Board of Trustees of The University of Illinois, Urban, Ill.

[21] Appl. No.: 915,896

[22] Filed: Jul. 17, 1992

Related U.S. Application Data

[60] Division of Ser. No. 521,119, May 3, 1990, Pat. No. 5,163,990, which is a continuation-in-part of Ser. No. 895,529, Aug. 11, 1986, Pat. No. 5,127,938, which is a continuation of Ser. No. 754,092, Jul. 15, 1985, abandoned, which is a continuation-in-part of Ser. No. 634,932, Jul. 27, 1984, abandoned.

[51] Int. Cl.$^5$ ............................................. A01N 37/02
[52] U.S. Cl. .................................... 504/171; 504/320
[58] Field of Search ................. 504/171, 162, 319, 320

[56] References Cited

U.S. PATENT DOCUMENTS

| | | | |
|---|---|---|---|
| 2,395,446 | 2/1946 | Benson | 504/320 |
| 3,043,675 | 7/1962 | Steinhards et al. | 71/94 |
| 3,274,206 | 9/1966 | Wilbert et al. | 71/94 |
| 3,804,845 | 4/1974 | Moore | 546/259 |
| 3,934,369 | 1/1976 | Rebeiz | 47/58 |
| 4,319,916 | 3/1982 | Abdulla | 71/94 |
| 4,322,241 | 3/1982 | Pissiotas et al. | 71/94 |
| 4,330,321 | 5/1982 | Johnston | 71/94 |
| 4,360,677 | 11/1982 | Doweyko et al. | 546/294 |
| 4,383,850 | 5/1983 | Handte et al. | 71/88 |
| 4,383,851 | 5/1983 | Rogers et al. | 71/94 |
| 5,127,938 | 7/1992 | Rebeiz | 504/319 |

FOREIGN PATENT DOCUMENTS

56845/60 1/1963 Australia .
56849/60 1/1963 Australia .

OTHER PUBLICATIONS

Arrese et al., Current Genetics, 7:175–183 (1983).
Ashton et al., _Mode of Action of Herbicides_, 2nd Ed. (John Wiley & Sons, NY), 1981.
Bazzaz et al., Photochemistry and Photobiology, 30:709–721 (1979).
Belanger et al., Spectrochimica Acta, 40A(9):807–827 (1984).
Belanger et al., Biochem., 19:4875–4883 (1980).
Belanger et al., Biochem., Biophys. Res. Comm., 88(2):365–372 (1979).
Belanger et al., Plant Science Letters, 18:343–350 (1980).
Belanger et al., J. Biol. Chem., 257(3):1360–1371 (1982).
Belanger et al., J. Biol. Chem., 257(9):4849–4858 (1982).
Belanger et al., J. Biol. Chem., 255(4):1266–1272 (1980).
Berestetskii et al., CA 93:198884c (1980).
Bickers et al., Biochem. Biophys. Res. Comm., 108(3):1032–1039 (1982).
Bioprocessing Technology, 8(2):3 (Feb. 1986).
Carey et al., Plant Physiol., 79:1–6 (1985).
Carey et al., Plant Physiol., 79:1059–1063 (1985).
Castelfranco et al., CA 81:22178p (1974).
Castelfranco et al., Plant Physiol., 53:615–618 (1974).
Chemical and Engineering News, Sep. 22, 1986, pp. 21–24.
Christensen et al., Br. J. Cancer, 48:35–43 (1983).
Cohen et al., Plant Physiol., 62:824–829 (1978).
Cohen et al., Plant Physiol., 67:98–103 (1981).
Cohen et al., Plant Physiol., 60:743–746 (1977).
Daniell et al., Biochem. Biophys. Res. Comm., 106(2):466–470 (1982).
Daniell et al., Biochem. Bioeng., 26:481–487 (1984).
Daniell et al., Biochem. Biophys. Res. Comm., 104(2):837–843 (1982).
Daniell et al., _Regulation of Chloroplast Differentiation_, 63–70 (Allan R. Liss, Inc. 1986).
Daniell et al., Biochem. Biophys. Res. Comm., 111(2):740–749 (1983).

(List continued on next page.)

_Primary Examiner_—Glennon H. Hollrah
_Assistant Examiner_—B. Bembenick
_Attorney, Agent, or Firm_—Curtis, Morris & Safford

[57] ABSTRACT

Plant defoliating compositions comprising δ-aminolevulinic acid and one or more chlorophyll biosynthesis modulators; and methods of making and using same.

12 Claims, 5 Drawing Sheets

OTHER PUBLICATIONS

Dickeson et al., J. Sci. Food Ag., 20:74–77 (1969).
Duggan et al., Biochem. Biophys. Acta, 714:248–260 (1982).
Duggan et al., Plant Science Letters, 24:27–37 (1982).
Duggan et al., Plant Science Letters, 27:137–145 (1982).
Duggan et al., Plant Physiol., 53(2):206–215 (1974).
Duggan et al., CA 80:129154j (1974).
Edwards et al., Neuroscience Letters, 50:169–173 (1984).
Ellefson, Mayo Clin. Proc., 57:454–458 (1982).
*Farming With Pride,* (Pride Company, Inc., P.O. Box 959 Minneapolis, Minn. 55440, 1986), pp. 11–13.
Fletcher et al., Weed Science, 32:722–726 (1984).
Freyssinet et al., Photobiochem. Photobiophys., 1:203–212 (1980).
Gassman et al., CA 83:203948b (1975).
Gough, *Light Stimulated δ-Aminolevulinate Accumulation in Luvulinate Treated Barley Seedings,* Carlsberg Res. Comm., 43:497–508 (1978).
Gough et al., CA 97:88590d (1982).
Hardt, CA 87:23068p (1977).
Hendry et al., CA 89:143401e (1978).
*Herbicide Handbook,* Beste, C. E., ed. (Weed Science Soc. of America, Champaign, Ill., 1983), pp. 1–469
*Herbicide Handbook,* Fifth Edition, 1983, pp. 362–366.
Rebeiz et al., Botany, 33:225–235 (1984).
Rebeiz, energy Research Symposium (Illinois Agricultural Exp. Station, University of Illinois, Champaign-Urbana, Feb. 5, 1981) pp. 9–12.
Rebeiz et al., In Regulation of Chloroplast Differentiation, 389–396 (Allan R. Liss, Inc. 1986).
Rebeiz et al., in *Thirty English Illinois Custom Spray Operators Training Manual (Symposium, Cooperative Extension Service, University of Illinois, Chanpaign-Urbana, College of Agriculture, Jan. 8–9, 1986), pp. 91–93.*
Rebeiz et al., in *Photosynthesis: Energy Conversion by Plants and Bacteria,* vol. I (Academic Press, Inc., 1982), pp. 699–780.
Rebeiz et al., Plant Physiol., 46:543–549 (1970).
Rebeiz et al., Enzyme Microb. Technol., 6:390 (Sep. 1984).
Rebeiz et al., Arch. Biochem. Biophys., 166:446–465 (1975).
Rebeiz, Illinois Research, 16(3):3–4 (1974).
Rebeiz et al., Plant Physiol., 47:24–32 (1971).
Rebeiz et al., Biotech and Bioeng. Symp. 8:453–471 (1978).
Rebeiz et al., Illinois Research, 21(1):3–4 (1979).
Rebeiz et al., Biochim. Biophys. Acta, 590:234–247 (1980).
Rebeiz et al., Plant Physiol., 40:281–286 (1965).
Rebeiz et al., Energy Research Symposium Proc. (University of Illinois, Champaign-Urbana, Apr. 27, 1982), pp .19–23.
Rebeiz et al., in *Photosynthesis V: Chloroplast Development* (G. Akoyunoglou, ed.) (Balaban International Science Services, Philadelphia, Pa., 1981) pp. 197–212.
Rebeiz, Chemtech., 12:52–63 (1982).
Rebeiz et al., Spectrochim. Acta, 40A(9):793–806 (1984).
Rebeiz et al., in *Regulation of Chloroplast Differentiation* (Allan R. Liss, 1986), pp. 13–24.
Rebeiz et al., Fluorescence Update (Perkin-Elmer Corp., Sep.-Dec. 1983) pp. 3–4.
Rebeiz, Bio Expo '85 (Boston, Mass., May 14–16, 1985), pp. 13–23.
Rebeiz et al., Mol. Cell Biochem., 57:97–125 (1983).
Rebeiz et al., Photochemistry, vol. 52, pp. 1099–1117 (1990).
Ruediger, Regulation of Chloroplast Differentiation, 3–12 (Allan R. Liss, Inc., 1986).
Sandberg et al., Photobiochem. and Photobiophys. 4:95–106 (1982).
Sandberg et al., Acta Dermatovener Suppl., 100:75–80 (1982).
Sisler et al., Physiol. Plant, 15:315–322 (1963).
Smith et al., Plant Physiol., 63:227–231 (1979).
Tetley et al., CA 83:75540y (1975).
Tripathy et al., Progress in Photosynthesis Research IV(8), 439–443, (Biggens, J., ed.) (1987).
Tripathy, J. of Biol. Chem., 261(29):13556–13564 (1986).
Tripathy et al., Anal. Biochem., 149:43–61 (1985).
Vermaas et al., CA 101(7):51954a (1984).
Vicek et al., CA 91:171842j (1979).
Wegler, *Chemie Der Planzenschutz–Und Schaedlingbekaempfungsmittel,* vol. 5 (Berlin, Germany, 1977), pp. 271–283.
Wu et al., Tetrahedron, 40(4):659–664 (1984).
Wu et al., J. Biol. Chem., 260(6):3632–3634 (1985).
Klein et al "Induction of d-Aminolevulinic Acid Formation . . . " Plant Physiol., vol. 60, 335–338, 1977.

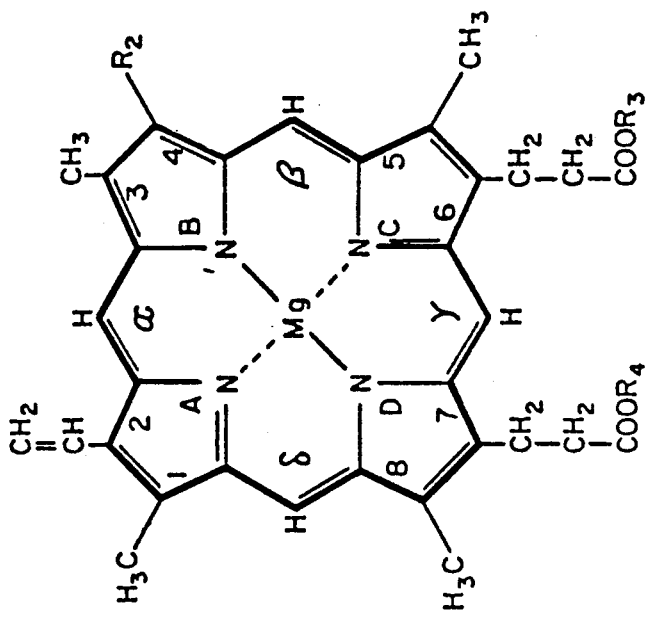

FIG. 2

1. Mg PROTO DIESTER, Mg PROTO MONOESTER AND Mg PROTO POOLS

A. $R_2=-CH=CH_2; R_3=-CH_3; R_4=F.Al; DV, 7\_FAl.E, 6Me.P, Mg PROTO (DV Mg PROTO DIESTER)$
B. $R_2=-CH_2-CH_3; R_3=CH_3; R_4=F.Al; 2\_MV, 7\_FAl.E, 6Me.P Mg PROTO (MV Mg PROTO DIESTER)$
C. $R_2=-CH=CH_2; R_3=-CH_3; R_4=H; DV, 7\_COOH, 6Me.P, Mg. PROTO (DV Mg PROTO 6ME)$
D. $R_2=-CH=CH_2; R_3=H; R_4=Alk; DV, 7\_Alk.E, 6\_COOH, Mg PROTO (DV Mg PROTO 7 ESTER)$
E. $R_2=-CH_2-CH_3; R_3=-CH_3; R_4=H, 2\_MV, 7\_COOH, 6Me.P, Mg PROTO (MV Mg PROTO 6ME)$
F. $R_2=-CH_2-CH_3; R_3=H; R_4=Alk.2\_MV.7Alk.E, 6\_COOH, Mg PROTO (MV Mg PROTO 7 ESTER)$
G. $R_2=-CH=CH_2; R_3=H; R_4=H; DV Mg PROTO$
H. $R_2=-CH_2-CH_2; R_3=H; R_4=H; 2\_MV Mg PROTO$

PHOTODYNAMIC PLANT DEFOLIANTS

The invention described herein was made in the course of work supported by grants from the U.S. Department of Agriculture, the National Science Foundation, the University of Illinois, the University of Illinois Agriculture Experiment Station and the John P. Trebellas Photobiotechnology Research Endowment.

This application is a division of application Ser. No. 07/521,119, filed May 3, 1990, now U.S. Pat. No. 5,163,990, issued Nov. 17, 1992, which is a continuation-in-part of application Ser. No. 06/895,529 filed Aug. 11, 1986, now U.S. Pat. No. 5,127,938 issued Jul. 7, 1992, which is a continuation of application Ser. No. 06/754,092 filed Jul. 15, 1985, now abandoned, which in turn is a continuation-in-part of application Ser. No. 06/634,932 filed Jul. 27, 1984, now abandoned.

FIELD OF THE INVENTION

This invention pertains to plant desiccating compositions and methods, and more particularly to plant desiccating compositions and methods for the induction of the accumulation of photodynamic tetrapyrroles in the foliage of plants.

BRIEF DESCRIPTION OF THE FIGURES

The following terms, as used hereinbelow, have the following meaning unless expressly stated to the contrary: Alk=($C_1$-$C_{10}$)alkyl group; ALA=δ-aminolevulinic acid; Chl=chlorophyll; Chlide a=chlorophyllide a; coprogen=coproporphyrinogen; cv=cultivar; dicot=dicotyledenous plant; DP=dipyridyl; DV=divinyl; E=ester; F.Al=fatty alcohol; LWMP=longer wavelength metalloporphyrins (the putative intermediates of ring E formation); M=methylation; ME=methyl ester; Me - methyl; Me.P=methylpropionate; monocot=monocotyledenous plant; MPE=Mg-protoporphyrin monoester; MP(E)=mixture of MPE and Mg-protoporphyrin IX; MV=monovinyl; P=esterification with geranyl geraniol, followed by stepwise conversion of the latter to phytol; PBG=porphobilinogen; Pchl= protochlorophyll; Pchlide=protochlorophyllide; Phy=phytol; Proto=protoporphyrin IX; Protogen=protoporphyrinogen IX; Urogen=uroporphyrinogen, var=variety.

The invention will be understood more clearly and fully with reference to the accompanying figures, in which:

FIG. 2 depicts representative structures of some of the metallotetrapyrroles ("tetrapyrroles") depicted in FIG. 1;

BACKGROUND OF THE INVENTION

Figure 1:
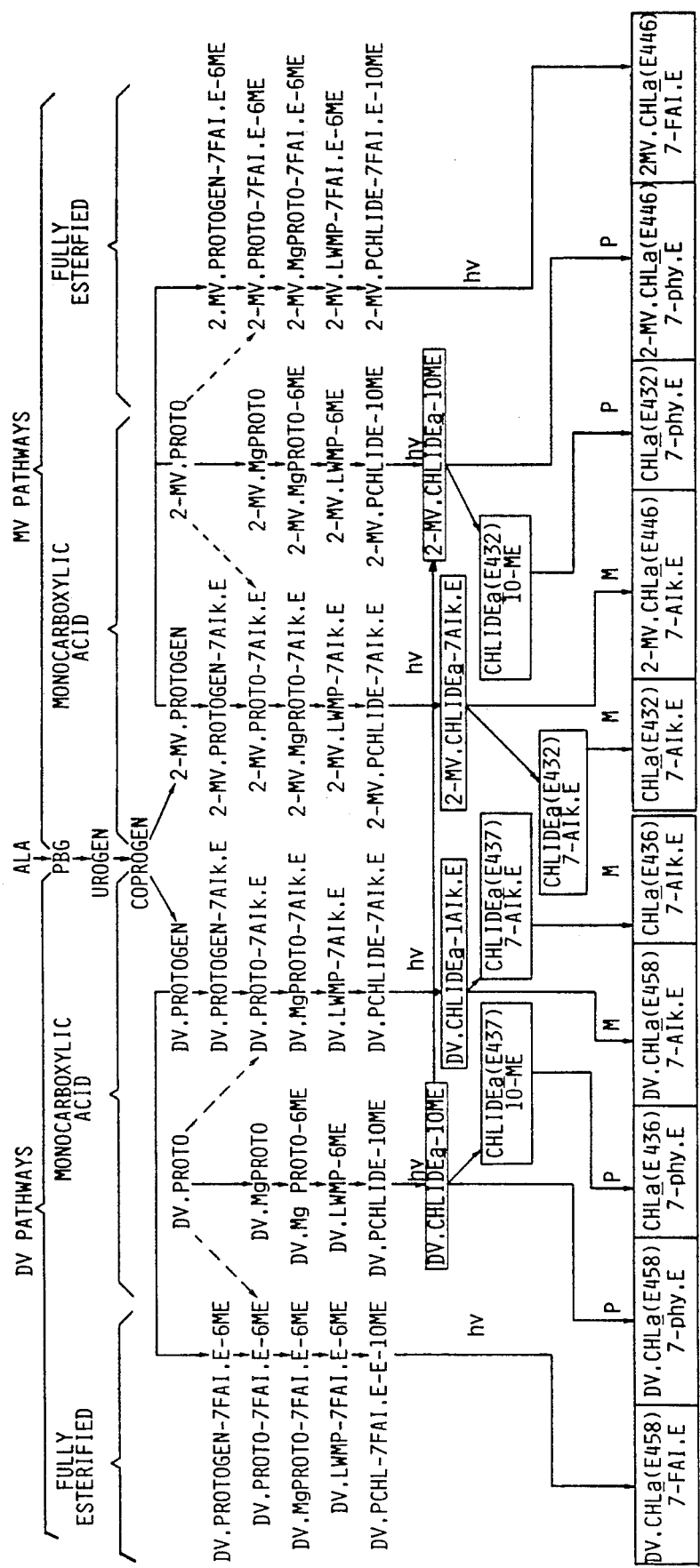
FIG. 1 depicts the six-branched Chl a biosynthetic pathway.

The timing and manipulation of plant development have some important implications in deciduous tree and crop production. Two important aspects in the manipulation of plant development are defoliation and fruit drop. First, controlled defoliation of nursery stock is essential for the effective management of rootstocks and grafted trees of both fruit and woody ornamental crops. For example, in areas with long growing seasons, nurserymen need to hasten defoliation in order to facilitate autumn digging. Autumn digging is a process whereby trees are dug out of the ground or "undercut" and then placed in cold storage. In order for a tree to be undercut and placed in cold storage, it must be dormant, i.e., it is not producing new shoots. Defoliation triggers dormancy in the tree which is followed by hardening of the tree. Hardening protects the tree from cold injury. Young apple trees are usually undercut and removed from the nursery in the fall and placed in cold storage. However, very often, trees in the nursery become juvenile by continuing to produce new shoots and retaining foliage longer through the season which retards hardening of the trees, making them more susceptible to cold injury. Therefore, it is desirable to hasten defoliation of the young trees.

Prior to the advent of chemical sprays or dust treatments, defoliation was done by hand, sometimes causing damage to shoots, bark, and buds. However, hand defoliation is time consuming and adds to the cost of a nursery operation. Furthermore, nutrients that would normally be translocated into the shoots during leaf senescence are lost.

Second, control of fruit drop is important in harvesting of fruit from trees. For example, aerial and subterranean fruits and vegetables are presently harvested either manually or mechanically. Manual harvesting is labor-intensive and expensive. Aerial mechanical harvesting of fruits uses heavy equipment that shakes the fruit off the tree. This in turn causes both soil compaction and frequent limb and trunk injury resulting in shorter tree life. Such mechanical harvesting also results in fruit damage in the form of bruises, cuts and punctures.

Various naturally occurring and non-naturally occurring chemical substances have been used for the purposes of defoliation and enhancement of fruit drop. In the case of fruit drop, chemicals are used to reduce fruit-pedicel attachment strength, thus allowing tree shakers to drop fruit more easily. However, chemical fruit harvesting has not been completely successful and has been used only in order to facilitate mechanical harvesting.

It would be a significant and useful advance in the art to have a chemical composition capable of causing defoliation and/or defoliation and fruit drop in plants, particularly deciduous fruit trees, via a mechanism involving one or more naturally occurring intermediates in the chlorophyll biosynthesis and which alleviates the disadvantages associated with present methods for defoliation and fruit drop.

Chlorophyll biosynthesis is a major biological phenomenon in the biosphere and is mandatory for the biosynthesis of photosynthetic membranes during greening and for the repair and maintenance of the Chl in mature green plants. The chlorophylis are a group of Mg-tetrapyrroles which in green plants catalyze the conversion of solar energy into chemical energy via the process of photosynthesis. There are two basic classes of chlorophyll, designated chlorophyll a (Chl a) and chlorophyll b (Chl b); Chl a is involved in the collection of solar energy and its conversion to chemical energy whereas Chl b is believed to be involved only in the collection of solar energy.

As shown in FIG. 1, ten species of Chl a are all synthesized via a multiple-branched pathway from one common precursor, δ-aminolevulinic acid (ALA), via a series of porphyrin, Mg-porphyrin, and protochlorophyll intermediates, collectively referred to as tetrapyrroles or tetrapyrrole intermediates (see FIG. 2).

As can be seen in FIG. 1, three of the branches of the synthetic pathway have been designated as divinyl (DV) pathways; the two monocarboxylic acid pathways predominate in dicots and in monocots in the presence of light. The remaining three branches have been designated the monovinyl (MV) pathways; the two monocarboxylic acid pathways predominate in monocots in the dark. Plants may be classified as "monovinyl" or "divinyl" plants, depending on which pathways predominate. A monovinyl plant is a plant species which in darkness accumulates MV Pchlide via the MV monocarboxylic acid biosynthetic routes and upon exposure to light initially forms Chl mainly via the MV monocarboxylic acid routes. Divinyl plants are plant species which accumulate mainly DV Pchlide in darkness and upon exposure to light initially form Chl preferably via the DV monocarboxylic biosynthetic routes. After several hours in daylight both MV and DV plants appear to form Chl via the DV monocarboxylic routes. This in turn has led to the classification of plants into four different greening groups (Rebeiz, C. A., Montazer-Zouhoor, A., Mayasich, J. M., Tripathy, B. C., Wu, S., and Rebeiz, C. C. *CRC Crit. Rev. in Plant Sci.*, 6:385-435 (1988)):

(a) Dark divinyl/light divinyl (DDV/LDV). In this greening group, chlorophyll formation proceeds via the DV-enriched protochlorophyllide pools at daybreak and in daylight.

(b) Dark monovinyl/light divinyl (DMV/LDV). In this greening group, chlorophyll formation proceeds via the MV-enriched protochlorophyllide pools at daybreak and via the DV-enriched protochlorophyllide pools in daylight.

(c) Dark monovinyl/light monoVinyl (DMV/LMV). In this greening group, chlorophyll formation proceeds via the MV-enriched protochlorophyllide pools in darkness and via the MV-enriched protochlorophyllide pools at daybreak and in daylight.

(d) Dark divinyl/light monovinyl (DDV/LMV). In this pathological greening group, chlorophyll formation proceeds via the DV-enriched protochlorophyllide pools at daybreak and via the MV-enriched protochlorophyllide pools in daylight.

As can be seen from FIG. 2, δ-aminolevulinic acid (ALA) is a 5-carbon amino acid. ALA is found in most living animal and plant cells and is the primary tetrapyrrole precursor. It is available from a variety of specialty chemical sources, e.g., Sigma Chemical Co., St. Louis, Mo. and Biosynth International, Skokie, Ill. It is known that excised plant tissues treated in the laboratory with small amounts of ALA will synthesize and accumulate Pchlide, which is the immediate precursor of Chlide a and of Chl a, and that ALA will induce the accumulation of earlier tetrapyrrole intermediates of the Chl biosynthetic pathway, such as coproporphyrin, Proto, and MP(E). Once the ALA has stimulated the synthesis of the tetrapyrrole intermediates, they are normally converted in the presence of sunlight into the various forms of Chl a, as described in FIG. 1. However, this rate-limiting conversion does not occur to any great extent in darkness; without sunlight, the tetrapyrrole intermediates accumulate in small amounts in their respective metabolic pools. Upon exposure to light, the conversion to Chl a resumes and the pools are depleted. In 1974, Castelfranco, P. A., Rich, P. M., and Beal, S. I., *Plant Physiol.* 53:615-618 noticed while studying the lag phase during greening of etiolated (dark grown) tissue that excised cucumber cotyledons soaked in ALA for 16 hours in the dark underwent visible tissue damage upon subsequent exposure to light, which was attributed to tetrapyrroles formed from exogenous ALA. This phenomenon was regarded as a nuisance to be avoided by illumination with red light of very low intensity or by illumination with intermittent light. It was believed that the accumulation of tetrapyrroles due to exogenous ALA was a phenomenon attributable to the peculiar circumstances of etiolation. Indeed, once the greening of etiolated tissue is initiated, the biosynthesis of chlorophyll proceeds at an abnormally high rate not found in normal green tissue.

Copending application Ser. No. 895,529, the disclosure of which application is expressly incorporated herein by reference, describes herbicidal compositions comprising one or more compounds selected from the group consisting of δ-aminolevulinic acid, inducers of δ-aminolevulinic acid synthesis in plants, enhancers of δ-aminolevulinic acid conversion to photodynamic tetrapyrroles in plants, and inhibitors of conversion of divinyl tetrapyrroles to monovinyl tetrapyrroles in plants; methods for inducing the accumulation of photodynamic tetrapyrroles in living plants using said compositions, and methods of controlling plants using said compositions. These compositions were discovered to have a herbicidal effect on plants as the result of the accumulation of tetrapyrroles in amounts greater than those normally found in the plants. This was surprising because mature green plants synthesize chlorophyll only at a rate sufficient to keep up with leaf expansion and repair, and it had not been previously believed that this rate would be sufficient to allow accumulation of amounts of tetrapyrroles large enough to result in photodynamic injury.

The accumulated tetrapyrroles photosensitize the formation of singlet oxygen, which is a very strong oxidant. The singlet oxygen rapidly oxidizes the lipoprotein components of the plant cellular membranes, thus setting in motion a highly destructive free-radical chain reaction, which can be summarized as follows (hv = photon of light; $^1$Tet = tetrapyrrole in the singlet ground state; $^3$Tet* = tetrapyrrole in the triplet excited state; $^3O_2$ = oxygen in the triplet ground state; $^1O_2$* = oxygen in the singlet excited state; UMLP = unsaturated membrane lipoproteins):

(1) $^1$Tet + hv → $^3$Tet*
(2) $^3$Tet* + $^3O_2$ → $^1$Tet + $^1O_2$*
(3) $^1O_2$* + (UMLP) → hydroperoxides
(4) hydroperoxides → free radicals
(5) free radicals + UMLP → more hydroperoxides
(6) repetition of steps (4) and (5) until most of the UMLP are oxidized.

While photosensitization by injected tetrapyrroles had been described in animals and human tissues (see, e.g., Ellefson, R. D., *Mayo Clinic Proc.* 57:454-458 (1982); Christensen, T., Sandquiet, T., Feren, K., Waksvik, H., and Moan, J., *Br. J. Cancer* 48:35-43 (1983);

Hopf, F. R., and Whitten, D. G., in *The Porphyrins,* Vol. 2, Dolphin, D., ed. (Academic Press, New York, 1978), pp. 161-195; Sandberg, S., Romslo, I., Hovding, G., and Bjorndal, T., Acta Dermatovener (Stockholm) Suppl. 100:75-80 (1982); Latham, P. S., and Bloomer, J. R., *Photochem. Photobiol.* 37:553-557(1983); Bickers, D. R., Dixit, R., and Mukhtar, H., *Biochem. Biophys. Res. Comm.* 108:1032-1039 (1982)), this phenomenon had not been demonstrated in whole green plants nor adapted to control undesirable susceptible plant species prior to the invention of Ser. No. 895,529.

OBJECTS OF THE INVENTION

It is therefore an object of the present invention to provide a photodynamic composition which is capable of defoliating a plant without killing the plant by causing the foliage to accumulate levels of tetrapyrroles which are higher than those normally found in the foliage.

It is a further object of the invention to provide a photodynamic composition for causing fruit drop in a plant, particularly in a deciduous fruit tree, without the need for mechanical harvesting.

It is yet another purpose of the invention to provide a photodynamic composition capable of causing defoliation and fruit drop in a plant.

It is another object of the invention to provide photodynamic compositions which are capable of defoliating and/or defoliating and causing fruit drop in a plant which are environmentally safe and efficient at low concentrations.

SUMMARY OF THE INVENTION

The invention is broadly directed to compositions for causing defoliation and/or fruit drop in whole, living plants and methods for defoliating and/or causing fruit drop in whole, living plants. Thus, in one embodiment, the invention is a plant defoliating composition comprising a plant defoliating effective amount of δ-aminolevulinic acid or δ-aminolevulinic acid in combination with one or more chlorophyll biosynthesis modulators and a suitable carrier.

In another embodiment, the invention is a plant defoliating composition comprising a plant defoliating effective amount of δ-aminolevulinic acid in combination with one or more chlorophyll biosynthesis modulators which are selected from the group consisting of inducers of δ-aminolevulinic acid synthesis, enhancers of δ-aminolevulinic acid conversion to tetrapyrroles and inhibitors of conversion of divinyl tetrapyrroles to monovinyl tetrapyrroles.

Another embodiment of the invention is a method for defoliating a plant comprising the steps of contacting the plant with a defoliating effective amount of δ-aminolevulinic acid, one or more chlorophyll biosynthesis modulators, or δ-aminolevulinic acid in combination with one or more chlorophyll biosynthesis modulators and allowing the contacted plant to be exposed to light.

In another embodiment, the invention is a method for defoliating a plant comprising the steps of contacting the plant with a defoliating effective amount of δ-aminolevulinic acid in combination with one or more chlorophyll biosynthesis modulators and allowing the contacted plant to be exposed to light.

In still another embodiment, the invention is a method for defoliating a plant comprising the steps of contacting the plant with a defoliating effective amount of δ-aminolevulinic acid, one or more chlorophyll biosynthesis modulators, or δ-aminolevulinic acid in combination with one or more chlorophyll biosynthesis modulators, exposing the contacted plant to a substantial absence of light at wavelengths of 300 to 700mM and then exposing the contacted plant to light.

A further embodiment of the invention is a composition for causing defoliation and fruit drop in a deciduous fruit tree comprising an amount effective to cause defoliation and fruit drop in a deciduous fruit tree of δ-aminolevulinic acid or δ-aminolevulinic acid in combination with one or more chlorophyll biosynthesis modulators and a suitable carrier.

Another embodiment of the invention is a composition for causing defoliation and fruit drop in a deciduous fruit tree comprising an amount effective to cause defoliation and fruit drop in a deciduous fruit tree of δ-aminolevulinic acid in combination with one or more chlorophyll biosynthesis modulators capable of causing the foliage of the tree to accumulate levels of tetrapyrroles which are selected from the group consisting of inducers of δ-aminolevulinic acid synthesis, enhancers of δ-aminolevulinic acid conversion to tetrapyrroles and inhibitors of the conversion of divinyl tetrapyrroles to monovinyl tetrapyrroles.

In a specific embodiment, the invention is a composition for causing defoliation and fruit drop in a deciduous fruit tree comprising an amount effective to cause defoliation and fruit drop in a deciduous fruit tree of δ-aminolevulinic acid in combination with ethyl nicotinate.

Still another embodiment of the invention is a method for causing defoliation and fruit drop in a deciduous fruit tree comprising the steps of contacting the tree with an amount effective to cause defoliation and fruit drop in the tree of δ-aminolevulinic acid, one or more chlorophyll biosynthesis modulators, or δ-aminolevulinic acid in combination with one or more chlorophyll biosynthesis modulators and allowing the contacted tree to be exposed to light.

A further embodiment of the invention is directed to a method for causing defoliation and fruit drop in a deciduous fruit tree comprising the steps of contacting a tree with an amount effective to cause defoliation and fruit drop in the tree of δ-aminolevulinic acid, one or more chlorophyll biosynthesis modulators, or δ-aminolevulinic acid in combination with one or more chlorophyll biosynthesis modulators, exposing the contacted tree to a substantial absence of light at wavelengths of 300 to 700 mM and then exposing the contacted tree to light.

DETAILED DESCRIPTION OF THE INVENTION

The invention will be understood more clearly and fully from the following detailed description.

It has now been discovered that foliage of whole, living plants can be induced by exposure to exogenous ALA to accumulate artificially high amounts of photodynamic tetrapyrrole intermediates in excess of levels normally found in foliage of living plants, and that such induced artificially high levels are sufficiently photodynamic so that subsequent exposure of the foliage to light causes desiccation and death of the foliage without killing the rest of the plant.

As a consequence of desiccation of the foliage of the plant, there is formation of an abscission layer between the branch and the leaf petioles (stems) which ultimately causes the leaves to fall from the branch. Similarly, desiccation of the foliage of fruit bearing plants, e.g., deciduous fruit trees, causes formation of an abscission layer between the branch and the fruit pedicel (stem) or the pedicel and the fruit which ultimately causes the fruit Co drop from the branch.

The foliage of a plant can be induced to accumulate tetrapyrroles because foliage is capable of synthesizing tetrapyrroles via the chlorophyll biosynthetic pathway. In contrast, "woody" parts of a plant, e.g., bark or stalk, do not actively synthesize tetrapyrroles and have sufficient carbohydrate reserves to recover from desiccation so that, notwithstanding desiccation of the foliage, the plant does not die.

As used herein, the term "plant" means a tree, shrub, seedling, or herb, which is a living organism and which typically does not exhibit voluntary motion or possess sensory or nervous organs.

The term "woody" as used herein refers to plant tissue which does not actively synthesize tetrapyrroles and includes ligneous tissues, i.e., tissue containing wood, wood fibers or wood-like fibers.

The term "herbaceous plant" refers to a plant having little or no woody tissue.

The term "deciduous tree" broadly refers to the opposite of evergreen tree and includes trees whose leaves fall off seasonally or at a certain stage of development in the life cycle.

As used herein, the term "young leaf" refers to a leaf which is still expanding in size.

As used herein, the term "mature leaf" refers to a leaf which has stopped expanding in size.

As used herein, the term "old leaf" refers to a mature leaf which is approaching senescence.

As used herein, the term "desiccate" means broadly to dry and includes loss of cellular fluids, followed by degradation of chlorophyll (Chl) and other biomolecules such as proteins, lipoproteins, and nucleic acids, and disintegration of subcellular organelles such as vacuoles, nuclei, mitochondria, plastids, microsomes and microbodies.

As used herein, the term "defoliate" means broadly to remove green plant tissue, in particular, foliage (leaves) and includes separation of leaves at their junction to petioles, or separation of leaves and petioles at their junction to branches, before or after complete leaf desiccation.

As used herein, the term "fruit drop" means broadly to remove fruit from branches of plants, in particular deciduous fruit trees, and includes separation of fruit at the junction to pedicels or separation of fruit and pedicels at their junction to branches before or after leaf desiccation.

As used herein, the term "fruit" means the mature ovary of a flower which includes either parts of the flower or inflorescence which are intimately associated with the mature ovary. Fruit includes but is not limited to apples, oranges, pears, peaches, cherries, tomatoes and the like.

As used herein, the term "chlorophyll biosynthesis modulator" refers to a compound other than exogenous ALA (ALA from sources outside the plant) which causes the green tissue of a plant, e.g.., foliage, to accumulate levels of tetrapyrroles which are higher than levels of tetrapyrroles normally found in untreated green tissue. Such modulators are selected from the group consisting of inducers of ALA synthesis, enhancers of ALA conversion to tetrapyrroles and inhibitors of conversion of divinyl tetrapyrroles to monovinyl tetrapyrroles. In accordance with the invention, one or more modulators, or one or more modulators in combination with ALA can be used to effect defoliation or defoliation and fruit drop in plants.

Modulators of the invention include, e.g., o-phenanthroline, 1,7-phenanthroline, 4,7-phenanthroline, and phenanthridine, available from, e.g., Alpha Products, Danvets, Mass.; 2,2'-dipyridyl (2,2'-DP), 2,3'-dipyridyl (2,3'-DP), 2,4'-dipyridyl (2,4'-DP), 1,7'-dipyridyl (1,7'-DP), 4,4'-dipyridyl (4,4'-DP), pyridine 2-aidehyde, pyridine 2-aldoxime, 2,2'-dipyridylamine, 2,2'-dipyridyl disulfide, 8-hydroxyquinoline, picolinic acid, nicotinic acid, 6-amino nicotinamide, ethyl nicotinate, 2-hydroxynicotinic acid, ethyl 2-methyl nicotinate, N-methyl nicotinamide, N-benzyl-N-nicotinoyl nicotinamide, 2-hydroxy-6-methylpyridine-3-carboxylic acid, 4-hydroxy-7-trifluoromethyl-3-quinoline carboxylic acid, 4-hydroxy-7-methyl-1,8-naphthyridine-3-carboxylic acid, diethyl 3,4-pyridine dicarboxylate, and niflumic acid, available from, e.g., Aldrich Chemical Co., Milwaukee, Wis.; and analogs thereof. Other modulators are listed in Table XVI below. It should be noted that nicotinic acid, an enzyme cofactor, occurs in all living cells and appreciable amounts are found in liver, yeast, milk, adrenal glands, white meat, alfalfa, legumes, whole cereals and corn. In addition, ethyl nicotinate is a vitamin derivative.

By "inducer of ALA synthesis" is meant a compound which, when applied to plants, stimulates the green tissue of the plant to produce a higher than normal amount of endogenous ALA ("native ALA," i.e., ALA normally found in a plant) which in turn causes accumulation of tetrapyrroles at levels sufficiently photodynamic so that upon subsequent exposure of the tissue to light, the tissue desiccates. Thus, an inducer results in a significant accumulation of a particular MV or DV tetrapyrrole when applied to a plant in the absence of exogenous ALA. Significant accumulation of a particular tetrapyrrole is defined as an amount of that accumulated tetrapyrrole which approaches or exceeds the net dark-conversion rate into that tetrapyrrole, brought about by a 5 mM exogenous ALA treatment. Furthermore, the inducer, in combination with ALA, results in the accumulation of higher levels of the particular MV or DV tetrapyrrole than when ALA or the inducer are applied to the plant separately. Thus, the compositions of the invention can comprise one or more inducers of ALA, or one or more inducers of ALA in combination with ALA.

By "enhancer of ALA conversion to tetrapyrroles" or "enhancer" is meant a compound which when applied to plants enhances the capability of the green tissues of the treated plants to convert exogenous or endogenous ALA to photodynamic tetrapyrroles. An enhancer does not result in a significant accumulation of a particular MV or DV tetrapyrrole when applied to a plant in the absence of exogenous ALA but, when used jointly with exogenous ALA, significantly enhances the dark conversion of exogenous ALA into the particular MV or DV tetrapyrroles over and beyond that caused by exogenous ALA alone, i.e., by ALA used as a control. A significant accumulation of a particular tetrapyrrole in this context is defined as the amount of that accumulated tetrapyrrole which approaches or exceeds the net dark-conversion rate into that tetrapyrrole brought about by a 5 mM exogenous ALA treatment. Enhancers of ALA conversion to tetrapyrroles fall into two groups: (1) enhancers of ALA conversion to MV Pchlide and (2) enhancers of ALA conversion to DV Pchlide and enhancers of ALA conversion to proto and MV- and DV-MPE. Thus, the compositions of the present invention can also comprise one or more enhancers of ALA, or one or more enhancers of ALA in combination with ALA or inducers of ALA.

By "inhibitor of the conversion of divinyl tetrapyrroles to monovinyl tetrapyrroles" is meant a compound which, when applied alone to plants, results in the inhibition of a particular MV tetrapyrrole in comparison to untreated controls and/or when applied to a plant in combination with ALA results in the inhibition of a particular MV tetrapyrrole in comparison to ALA-treated controls.

A modulator which functions as one of type of modulator (i.e., inducer, enhancer or inhibitor) in a specific plant or at a given concentration may function as a different type of modulator at a different concentration or in another plant, although a compound which is a modulator in one type of plant will be a modulator in most other types of plants.

For example, 2,2'-dipyridyl can be an enhancer in cucumber at concentrations less than 20 mM but can also be an inducer in cucumber at concentrations of 20mM or greater. Further, in cucumber, a DDV/LDV plant species, 2,2'-dipyridyl and o-phenanthroline are inducers; pyridine 2-aldoxime, pyridine 2-aidehyde, picolinic acid, 2,2'-dipyridyl disulfide, 2,2'-dipyridylamine, 4,4'-dipyridyl, phenanthridine, nicotinic acid, 2-hydroxynicotinic acid, 2-hydroxy-6-methylpyridine-3-carboxylic acid, ethyl nicotinate, ethyl-2-methyl nicotinate and 4-hydroxy-7-trifluoro-8-quinoline carboxylic acid are enhancers; and 2,3'-dipyridyl, 2-4'-dipyridyl, 1,7-phenanthroline, 4,7-phenanthroline, diethyl 3,4-pyridine dicarboxylate and niflumic acid are inhibitors; in soybean, a DMV/LDV plant species, 2,4-dipyridyl, 2,2'-dypiridylamine, phenanthridine, picolinic acid, pyridine 2-aldoxime, 2,3-dipyridyl, 4,4'-dipyridyl, 1,7-dipyridyl, pyridine 2-aidehyde, 2,2'-dipyridyl disulfide and 8-hydroxyquinoline are enhancers; and 4,7-phenanthroline and 1,7-phenanthroline are inhibitors; and in Johnsongrass, a DMV/LMV plant species, 2,2'-dipyridylamine, pyridine 2-aldoxime, pyridine 2-aidehyde, picolinic acid, 2,2'-dipyridyl, 2,4-dipyridyl, 1,7-phenanthroline, 2,2'-dipyridylamine, 2,2'-dipyridyldisulfide, 2,3-dipyridyl and 4,7-phenanthroline are enhancers; and 2,4-dipyridyl and 2,3-dipyridyl are inhibitors. One skilled in the art will be able to determine, without undue experimentation, whether a compound is a modulator and, if desired, will be able to determine the type of modulator based on the methods disclosed herein.

Thus, the compositions of the present invention can also comprise combinations of ALA and one or more chlorophyll biosynthesis modulators selected from the group consisting of inducers, enhancers, and inhibitors, e.g., ALA+one or more inducers, ALA+one or more enhancers, ALA+one or more inhibitors, ALA+one or more inducers+one or more enhancers, ALA+one or more inducers+one or more inhibitors, ALA+one or more enhancers+one or more inhibitors, ALA+one or more inducers+one or more enhancers+one or more inhibitors, etc.

A consideration of one or more of the following factors will enable one skilled in the art to effect the desired defoliation and/or fruit drop for a given plant species: the species of the plant (monocot, dicot, annual, perennial, woody, non-woody); the age of the plant; the various tissues types present on the plant (cotyledons; stems, leaves, leaf petioles, growing points, fruit pedicels, bark, etc.); and the point of time in the growing season. For example, (a) spraying a plant with woody branches will result in the desiccation of the green leaves but not the woody branches because the woody branches are protected by suberized bark which does not respond to treatment by accumulating tetrapyrroles; (b) spraying a young plant with tender, succulent stems containing chlorophyll will desiccate both the leaves and the stems, while treatment of plants with branches protected by suberized bark will result in desiccation of the leaves only; (c) spraying stems containing green leaves and unprotected growing points (e.g., leaf and flower buds) will desiccate both the leaves and the growing points, while spraying stems with leaves and growing points protected by suberized scales will only desiccate the leaves leaving the protected growing points unaffected; (d) spraying plants with young and old leaves may result in the desiccation of a larger proportion of the old or young leaves, depending on the nature of the modulator (i.e., inducer, enhancer or inhibitor) used with ALA; (e) spraying an annual plant with few carbohydrate reserves will result in desiccation followed by a slower rebound than a perennial plant with more carbohydrate reserves; and (f) spraying a woody plant, with carbohydrate reserves stored in the woody stems and roots, at the end of the growing season will result in desiccation of the leaves without resprouting of new leaves, while spraying the same plant early in the growing season will result in desiccation of the treated leaves, but with regeneration of new leaves from the carbohydrate reserves stored in the stems and roots, given proper temperature and daylength conditions.

The compositions of the present invention can contain one or more of the following: suitable carrier(s) (e.g., colloidal magnesium aluminum silicate, pumice, talc, or combinations thereof); solvent(s) (e.g., water, 0.45 acetone: 0.45 ethanol:0.1 Tween 80:9 water (v/v/v/v), 0.45 acetone:0.45 methanol:0.1 Tween 80:9 water (v/v/v/v), 0.1-1% Tween 80 in water (v/v), 0.9 polyethylene glycol (PEG):0.1 Tween 80:9 water (v/v/v), 0.1-0.7 PEG:0.2--0.8 methanol:0.1 Tween 80:9 water (v/v/v/v), 0.9 methanol:0.1 Tween 80:9 water (v/v/v), 0.45 acetone:0.45 ethanol:0.2 Tween 80:0.9 ethylene glycol:18 water (v/v/v/v/v), or one or more of the following: benzene, toluene, xylene, kerosene, 2-methoxyethanol, propylene glycol, diethylene glycol, diethylene glycol diethyl ether, formamide, methylformamide, cyclohexanone, isophorone); buffer(s) (e.g., citric acid); wetting agent(s) (e.g., sodium N-methyl-N--oleoyltaurate, an alkylphenoxy polyoxyethylene ethanol, sodium olefin sulfonate, sodium isopropylnaphthalene sulfonate, polyoxyethylated vegetable oil); dispersing agent(s) (e.g., sodium lignin sulfonate, the sodium salt of a naphthalene sulfonic acid-formaldehyde condensate, hydroxyethyl cellulose); defoaming agent(s) (e.g., silicone); emetic(s) (e.g., sodium tripolyphosphate, tetra potassium pyrophosphate, arecotine, apomorphine, copper sulfate); stench(es) (e.g., pyridine); penetrant(s); surfactant(s); emulsifier(s); and adjuvant(s) (e.g., phytoblend oils). Of course, any such additional component must be compatible with the active ingredients of the present invention and with the other ingredients in the mixture.

The compositions can be formulated in any manner conventionally used for plant preparations, e.g., as a solution, suspension, emulsion, flowable concentrate, emulsifiable concentrate, gel, paste, foam, cream, aerosol, wettable powder, dust, dispersible granules, and the like, according to procedures known to those skilled in the art. Advantageously, the composition is a solution, suspension, emulsion, aerosol, flowable or emulsifiable concentrate, or wettable powder. Of course, the formulation must be such that the active ingredient(s) penetrate(s) the plant tissue and translocates to the sites of tetrapyrrole synthesis. When the compositions are made in solution they can conveniently comprise concentrations of from about 1 to about 40 mMALA, advantageously, 15 mM to 40 mM, and from about 5 to about 30 mM inducer, enhancer, or inhibitor, advantageously 15 to 30 mM.

The compositions of the present invention can be applied topically, e.g., as a dust, soak, dip, spray, mist, or fog, in an amount sufficient to induce the accumulation of photodynamic tetrapyrroles. Alternatively, the compositions can be applied to the soil for uptake by plant roots and translocation to the vegetative part of the plant. The amount of composition to be applied will vary, depending on the particular active ingredient(s) selected, but in general will be an amount sufficient to supply from about 10 g to about 15 kg ALA per acre and/or from about 10 g to about 10 kg of an inducer, enhancer, or inhibitor per acre. Means of determining optimum application rates are within the purview of those skilled in the art.

Once the tissues of the plant have been induced to begin accumulating artificially high amounts of tetrapyrroles by exposure to the compositions of the present invention, the plant may be shielded from exposure to light to allow maximum tetrapyrrole accumulation. Such dark incubation is not required for activity but tends to optimize efficiency of the compositions. The plants can be shielded in any convenient manner, as by wrapping them in dark paper, cloth, or foil, or by placing them in a dark room or container. Under field conditions, the ideal method to provide a period of dark incubation is to apply the composition at dusk or during the night, at a time chosen to allow the plants to rest in the dark for at least one hour. It is to be understood that in order to facilitate tetrapyrrole accumulation, the dark need not be total absence of light, but rather substantial absence of light at wavelengths of from 300 to 700 nm. Advantageously, the plants are allowed to rest in the dark for from about 1 to about 20 hours. One to 8 hours is particularly advantageous.

Thereafter the plants are exposed to about 200 ft. candles or more of light at wavelengths of about 300 to about 700 nm. The light can be supplied by any convenient source, e.g., an incandescent lamp, metal halide lamp, sunlamp, or a cool white or skylight fluorescent bulb. In the field, of course, the preferred source of light is sunlight. The plants are exposed to light for a period of time sufficient to oxidize most of the unsaturated membrane lipoproteins; a period of from about 1 to about 14 days is preferred.

A further understanding of this invention can be had from the following illustrative examples. Desiccating activity is indicated by tissue necrosis and leaf abscission and/or fruit drop. As used hereinabove and below unless expressly stated to the contrary, all temperatures and temperature ranges refer to the centigrade system and the terms ambient and room temperature refer to about 20°–25° C. The term percent or (%) refers to weight percent and the terms mole and moles refer to gram moles. "Level of significance" refers to the probability that for a population for which the correlation coefficient (r) is equal to zero, a sample of size n can be taken, for which the correlation coefficient equals or exceeds the calculated value of r reported for the given sample. The abbreviation "n.s." stands for "not significant".

SECTION I

PROTOCOL FOR DETERMINING PHOTODYNAMIC DEBICCATING COMPOSITIONS

The following examples describe model systems whereby persons skilled in the art can readily determine photodynamic compounds and compositions useful in the present invention.

EXAMPLE 1 photodynamic Effects of ALA

Cucumber (*Cucumis sativus* L. cv Beit Alpha MR) seedlings were germinated in the greenhouse in vermiculite in glass containers, 9 cm deep and 9 cm in diameter. The seedlings were watered periodically with Hoagland solution. The photoperiod was maintained at 14 hours of light per day with 50 ft. candles of incandescent light.

Six-day old green seedlings were thinned to 10 plants per container and ALA (Sigma Chemical Co., St. Louis, Mo.) was applied as a fine spray. The ALA was dissolved at concentrations ranging from 0 to 20 mM in a solvent mixture made up of 0.45 acetone:0.45 ethanol:0.1 Tween 80:9 water (v/v/v/v), adjusted to pH 3.5 with dilute HCl. Each 9 cm-diameter glass container (approximately 63.6 $cm^2$ leaf surface area) was sprayed with 0.25 ml of ALA (treated) or 0.25 ml of solvent (control), which is equivalent to a spray rate of about 40 gallons/acre and a field application rate of ALA of about 0 to 524 g/acre. The solutions were delivered as a very fine and uniform spray with a modified Pierce "Quixspray" aerosol spray kit (Pierce Chemical Co., Rockford, Ill.), as follows: 0.25 ml of solution was placed in a sawed-off 10 ml conical centrifuge tube, which was placed inside the Quixspray spray jar. The delivery of a very fine mist was achieved by pumping the solution through a fine bore polypropylene tubing (0.3 mm inside diameter, or 0.5 mm inside diameter for more viscous solutions). One end of the fine-bore tubing was inserted into the Quixspray intake hose, while the other end was dipped into the solution in the conical centrifuge tube. In this manner it took 10–20 sec to deliver 0.25 ml spray, and this in turn provided ample time for thoroughly spraying the seedlings to leaf saturation. Each treatment was performed in duplicate. Average droplet size diameter was approximately 25 $\mu$m for the 0.3 mm tubing and about 50 $\mu$m for the 0.5 mm tubing.

After spraying, the plants were wrapped in aluminum foil and were placed inside a cardboard box which was wrapped in two layers of black plastic. The dark-boxes were then incubated overnight (17 hours) at 28° C., in order to allow the biosynthesis and accumulation of tetrapyrroles to take place.

The next morning, the treated plants were sampled for their tetrapyrrole content. The plants were taken in the black boxes to a dark room equipped with a green safelight which permits the manipulation of the treated tissues without affecting in any way their tetrapyrrole content. One of each two cotyledons of every two replicates was excised. Two- to three-gram batches were then homogenized in a Sorval Omnimixer (DuPont Instruments, Newtown, Conn.) in acetone:0.1N NH4OH (9:1 v/v) at a rate of 18 ml of solvent per 3 g of tissue. The resulting 80% acetone extract containing various tetrapyrroles was cleared from lipoproteins and cell debris by centrifugation at 39,000 × g for 10 min at 0° C. Chlorophyll, a fully esterified tetrapyrrole, was removed from the aqueous acetone solution by extraction with hexane according to the method of Rebeiz, C. A., Mattheis, J. R., Smith, B. B., Rebeiz, C. C., and Dayton, D. F. *Arch. Biochem. Biophys.* 166:446–465 (1975). The more polar mono- and dicarboxylic tetrapyrroles such as Proto, MP(E), and Pchlide remained in the hexaneextracted aqueous acetone fraction. The chemical structure of these tetrapyrroles has been discussed at length in Rebeiz, C. A. and Lascelles, J., in *Photosynthesis: Energy Conversion by Plants and Bacteria*, Vol. 1, Govindjee, ed. (Academic Press, New York, 1982), pp. 699–780; and Rebeiz, C. A., Wu, S. M., Kuhadja, M., Danjell, H., and Perkins, E. J. *Mol. Cellular BioChem.* 57:97–125 (1983). The amount of Proto, MP(E), and Pchlide was determined spectrofluorometrically on aliquots of the hexane-extracted acetone fraction according to the method of Rebeiz, C. A., Mattheis, J. R., Smith, B. B., Rebeiz, C. C., and Dayton, D. F., *Arch. Biochem. Biophys.* 171:549–567 (1975). A small aliquot of the hexane extract containing the Chl a and b was dried under $N_2$ gas and the residue was redissolved in 80% acetone. The amount of Chl a and b in this acetone solution was then determined spectrofluorometrically according to the method of Bazzaz, M. B., and Rebeiz, C. A., *Photochem. Photobiol.* 30:709–721 (1979).

Fluorescence spectra were recorded on a fully corrected photon counting spectrofluorometer Model SLM 8000 DS (SLM-Aminco, Urbana, Ill.) equipped with two red-sensitive, extended $S_{20}$ photomultipliers (EMI 9658), and interfaced with a microcomputer system Model 9825 S (Hewlett-Packard, Sunnyvale, Calif.). Tetrapyrrole solutions were monitored at room temperature on 0.3 ml samples, in cylindrical microcells, 3 mm in diameter. Conversion of the digital spectral data into concentrations was performed automatically by the microcomputer, following the recording of the pertinent spectra, according to the method of Rebeiz, C. A., Daniell, H., and Mattheis, J. R., *Biotech. Bioeng. Symp. No.* 12:413–439 (1982). The emission and excitation spectra were recorded at excitation and emission bandwidths of 2 mm.

Monovinyl tetrapyrroles were distinguished from divinyl tetrapyrroles by their well-established spectrofluorometric properties in ether at 77 ° K. (see Rebeiz and Lascelles, supra; Rebeiz, Wu, Kuhadja, Daniell and Perkins, supra; Belanger, F. C., and Rebeiz, C. A., *J. Biol. Chem.* 257:1360–1371 (1982); and Belanger, F. C., Duggan, J. X., and Rebeiz, C. A., *J. Biol. Chem.* 257:4849–4858 (1982)). The low temperature fluorescence emission and excitation spectra were recorded in cylindrical sample tubes as described in Cohen, C. E., and Rebeiz, C. A., *Plant Physiol.* 61:824–829 (1978).

Absorption spectra were recorded with an Aminco dual wavelength spectrophotometer model DW-2 (SLM-Aminco, Urbana, Ill.) operated in the split-beam mode, at a slit width of 2 nm.

The acetone-insoluble residue which was left behind after centrifugation of the tissue homogenate was suspended in distilled water with an all glass tissue grinder. Total proteins were determined on a small aliquot of the suspension, after delipidation, according to the method of Rebeiz, C. A., Castelfranco, P. A., and Engelbrecht, A. H., *Plant Physiol.* 40:281–286 (1965).

After 17 hours of dark- incubation the treated plants accumulated 382.82 and 2.36 nmoles of Pchlide and MP(E), respectively, per 100 mg protein, above and beyond the controls. The seedlings with half of their cotyledons still intact were then used for assessing photodynamic damage by light. The seedlings were exposed to daylight in the greenhouse (400 to 5000 ft. candles at noon, depending on cloud cover) and their growth was evaluated over a period of 10 days. In order to secure a permanent record of the growth behavior of the treated plants, the latter were photographed daily (Kodacolor, 400 ASA, Eastman Kodak Co., Rochester, N.Y.) with a Pentax Super Program camera (Helix, Champaign, Ill.) equipped with an SMC Pentax-A 1:1.4 50 mm lens and a digital back that imprinted on each photograph the date or time of day at which the photograph was taken. Per cent photodynamic damage was assessed as the percent death of the sprayed tissue, in response to exposure to sunlight. For example, if 10 out of 10 sprayed leaves or cotyledons died as a consequence of exposure to daylight, the photodynamic damage was considered to be 100%. If only five out of the ten sprayed leaves or cotyledons had died, the photodynamic damage was considered to be only 50%, etc.

The extent of photodynamic damage was related to the amount of accumulated tetrapyrroles by conventional correlation analysis. The amounts of tetrapyrrole that accumulated were expressed in nmoles per 100 mg of tissue protein.

The results of these experiments are shown in Table I.

TABLE I

| Experiment[1] | Treatment | | Various Concentrations of ALA change[2] after 17 h of dark-incubation nmol/100 mg protein | | | | Photodynamic damage (%) |
|---|---|---|---|---|---|---|---|
| | mM ALA | g/acre | Pchlide | MP(E) | Proto | Tetrapyrroles[3] | |
| A | 0(Control) | 0 | 0.00 | 0.00 | 0.00 | 0.00 | 0 |
| | 5 | 131 | 31.77 | −4.44 | −17.33 | 10.00 | 22 |
| | 10 | 262 | 132.76 | −0.50 | −13.07 | 119.19 | 45 |
| | 15 | 393 | 271.29 | 1.23 | −17.33 | 255.19 | 95 |
| | 20 | 524 | 210.60 | −0.75 | −17.33 | 192.52 | 85 |
| | Correlation coefficient | | 0.988 | | | 0.978 | |
| | Level of significance | | 0.1% | | | 0.1% | |
| B | 0(Control) | 0 | 0.00 | 0.00 | 0.00 | 0.00 | 0 |
| | 1 | 26 | 24.95 | −3.08 | −2.81 | 61.12 | 2 |
| | 5 | 131 | 140.82 | −1.69 | −12.41 | 123.72 | 63 |
| | 10 | 262 | 147.82 | 3.83 | 19.58 | 168.23 | 92 |

TABLE I-continued

| Experiment[1] | Treatment | | change[2] after 17 h of dark-incubation nmol/100 mg protein | | | | Photodynamic damage (%) |
|---|---|---|---|---|---|---|---|
| | mM ALA | g/acre | Pchlide | MP(E) | Proto | Tetrapyrroles[3] | |
| | 15 | 393 | 191.22 | 0.78 | −12.41 | 175.03 | 95 |
| | Correlation coefficient | | 0.998 | | | 0.975 | |
| | Level of significance | | 0.1% | | | 0.1% | |

[1] In experiment A, the light intensity at noon during the first day of exposure to daylight was about 400 ft. candles. In experiment B, it was about 5000 ft. candles.
[2] The change in tetrapyrrole concentration is the difference between the tetrapyrrole content of the ALA-treated plants and that of the control plants which were sprayed with the solvent only, i.e. without added ALA, after 17 h of dark incubation and just prior to exposing the plants to daylight. The control plants contained the following amounts of tetrapyrrole after 17 h of dark incubation, and prior to exposure to daylight: A: 99.6, 7.66, 17.33 and B: 22.69, 6.96, and 12.41 nmo le Pchlide, MP(E) and Proto respectively per 100 mg protein.
[3] = Pchlide + MP(E) + Proto The symptoms of photodynamic damage assumed two forms: bleaching of the green leafy tissue, which spread gradually; and severe bleaching of the hypocotyl. In both cases, this was accompanied by a severe loss of turgidity of the affected tissues. The photodynamic damage was effected on the cell membranes which became leaky and this in turn resulted in a rapid and severe dehydration of the tissues. For example, at ALA concentrations of 10-20 mM (262-524 g/acre) a large number of seedlings had undergone irreversible damage after four to five hours of exposure to daylight. The cause of death was usually due to severe dehydration, bleaching, and collapse of the leafy and/or hypocotyl tissues. On the other hand, treated samples kept for the same period of time in darkness were unaffected.

EXAMPLE 2

Photodynamic Response of Various Plant Species to ALA+2,2'-DF Treatment

The procedure of Example I was performed on the following representative monocots and dicots:
Cucumber (Cucumis Sativus L. cv Beit Alpha MR)
Lambsquarter (Chenopodium album)
Mustard (Brassica kaber/juncea)
Red root pigweed (Amaranthus retroflexus)
common purslane (Portulaca oleracea)
Tomato (Lycopersicon esculentum cv Jet Star)
Cotton (Gossypium herbacium cv Coker-315)
Red kidney bean (Phaseolus vulgaris L. cv. California Dark Red)
Soybean (Glycine max cv Williams)
Perennial bluegrass (Poa pratensis cv Aspen)
Barley (Hordeum vulgare, var. Beacon Spring)
Sweet corn (Zea mays L. cv Gold Cup)
Crabgrass (Digitaria sanguinalis L. and Digitaria ischaemum)
Giant foxtail (Setaria faberii)
Oat (Arena satira cv Centennial)
Wheat (Triticum sativum cv Auburn)

The greenhouse-grown seedlings were treated with 0.25 ml of 5 mM (131 g/acre) ALA+15 mM (402 g/acre) 2,2'-DP, pH 3.5. Controls were treated with solvent only. All plants were then incubated in the dark for 17 hours. The next morning the seedlings were sampled in the dark for tetrapyrrole content using the procedure of Example I for dicots and the following procedure for monocots: the seedlings of one of the two replicates were excised into an upper half and a lower half. The two batches of excised tissue were then homogenized separately in a Sorval Omnimixer in acetone:0.1N NH₄OH (9:1 v/v) at a rate of 18 ml of solvent per 3 g of tissue. The other replicate was used to assess the photodynamic effect of light on the seedlings. For some dicots, the stems as well as the leaves were analyzed for tetrapyrroles. The results are given in Table II:

TABLE II

| | | | Photodynamic Response of Various Plant Species to ALA + 2,2'-DP Spray | | | | | | |
|---|---|---|---|---|---|---|---|---|---|
| | Age at | Type of | | | nmol/100 mg protein | | | | Photodynamic |
| | spraying | herbicidal | PChlide | | MP(E) | | Proto | | damage (%) |
| Plant | (days) | response[1] | Control | Treated | Control | Treated | Control | Treated | Control | Treated |
| Cucumber cotyledons | 6 | I | 84.79 | 434.12 | 8.51 | 68.85 | 3.64 | 19.06 | 0 | 85 |
| Cucumber stems | 6 | I | 10.87 | 71.77 | 5.32 | 14.47 | 12.67 | 39.37 | 0 | 85 |
| Lambsquarter | 7 | I | 23.52 | 72.58 | 3.83 | 33.94 | 17.59 | 13.87 | 0 | 100 |
| Mustard leaves | 12 | I | 29.84 | 200.82 | 12.01 | 36.11 | 29.08 | 23.52 | 0 | 90 |
| Mustard stems | 12 | I | 15.26 | 49.60 | 2.95 | 13.13 | 0.00 | 38.35 | | |
| Red root pigweed | 11 | I | 29.47 | 59.08 | 1.64 | 20.59 | 0.00 | 2.90 | 0 | 95 |
| Common purslane | 21 | I | 8.37 | 33.30 | 1.54 | 11.79 | 1.88 | 5.71 | 0 | 80 |
| Tomato cotyledons | 13 | I | 27.19 | 114.86 | 0.69 | 34.40 | 0.31 | 0.31 | 0 | 90 |
| Tomato stems | 13 | I | 3.69 | 14.26 | 0.82 | 2.53 | 0.00 | 0.00 | 0 | 90 |
| Cotton cotyledons | 14 | II | 18.06 | 36.53 | 3.95 | 9.22 | 0.00 | 0.00 | 0 | 63 |
| Cotton stems | 14 | II | 3.70 | 4.18 | 1.19 | 1.13 | 0.00 | 0.00 | 0 | 0 |
| Kidney bean leaves | 9 | II | 117.03 | 438.79 | 3.11 | 430.12 | 4.88 | 21.42 | 0 | 100 |
| Kidney bean stems | 9 | II | 36.78 | 82.26 | 3.89 | 75.90 | 3.49 | 14.2 | 0 | 0 |
| Soybean leaves | 9 | II | 25.31 | 98.88 | 3.61 | 105.84 | 4.24 | 10.87 | 0 | 78 |
| Soybean stems | 9 | II | 6.06 | 6.17 | 0.37 | 0.45 | 0.00 | 0.45 | 0 | 0 |
| Perennial bluegrass | 18 | II | 9.87 | 39.46 | 0.39 | 43.52 | 0.54 | 51.46 | 0 | 30-40 |
| Barley | 6 | III | 12.69 | 58.64 | 0.8 | 3.39 | 0.39 | 1.11 | 0 | S.N.[2] |
| Corn | 9 | III | 79.09 | 85.44 | 4.90 | 15.47 | 12.39 | 0.00 | 0 | S.N. |
| Crabgrass | 25 | III | 44.43 | 114.32 | 3.13 | 27.63 | 0.00 | 0.00 | 0 | S.N. |
| Giant foxtail | 6 | III | 7.87 | 78.75 | 0.44 | 11.91 | 0.00 | 13.92 | 0 | S.N. |
| Oat upper half | 7 | III | 29.19 | 171.96 | 13.02 | 23.04 | 0.00 | 0.00 | 0 | S.N. |
| Oat lower half | 7 | III | 92.53 | 121.86 | 9.37 | 3.84 | 0.00 | 0.00 | 0 | 0.0 |

TABLE II-continued
Photodynamic Response of Various Plant Species to ALA + 2,2'-DP Spray

| Plant | Age at spraying (days) | Type of herbicidal response[1] | PChlide Control | PChlide Treated | nmol/100 mg protein MP(E) Control | MP(E) Treated | Proto Control | Proto Treated | Photodynamic damage (%) Control | Treated |
|---|---|---|---|---|---|---|---|---|---|---|
| Wheat upper half | 7 | III | 29.58 | 101.25 | 8.34 | 5.22 | 9.96 | 0.60 | 0 | S.N. |
| Wheat lower half | 7 | III | 31.87 | 47.23 | 2.10 | 0.99 | 0.00 | 0.00 | 0 | 0.0 |

[1]These types of photodynamic response are discussed below.
[2]S.N. = small necrotic areas.

An examination of results of this survey revealed that plants reacted in three different ways to the ALA+2,2'-DP spray. One group of dicots, which is exemplified by cucumber, exhibited what is referred to as Type I herbicidal response in Table II. This group of plants reacted to the ALA+2,2'-DP spray exactly as did cucumber. Leafy tissues, stems and growing points accumulated significant amounts of tetrapyrroles and were subject to severe photodynamic damage (Table II). Usually, the seedlings died very rapidly, and the rapidity of the response depended on the light intensity in the greenhouse. For example, at the low spray concentrations used in this work (131 g/acre ALA+402 g/acre 2,2'-DP), only 4 to 5 hours of exposure to daylight was sufficient to cause the death of the plants on clear, bright days (4000 to 6000 ft. candles at noon). On the other hand, 2 to 3 days of insolation were required on very cloudy days (400 ft. candles at noon) in order to achieve the same results. Some of the plant species that exhibited this type of photodynamic herbicidal response such as lambsquarter, mustard, redroot pigweed and common purselane are considered to serious weeds. While 13-day old tomato plants, with fully expanded cotyledons and with small developing primary leaves exhibited a Type I response (Table II), younger 8- to 10-day old tomato seedlings were much less affected by the spray (approximately 40% photodynamic damage).

Other dicots such as cotton, kidney bean and soybean exhibited a different response to the ALA+2,2-DP treatment. This response is referred to as Type II in Table II. Plants belonging to this group accumulate significant amounts of tetrapyrroles in the leafy tissues, but not in the stems as in cotton and soybean. Other species such as kidney bean also accumulated some tetrapyrroles in the stems. Leaves that accumulate tetrapyrroles exhibit very severe photodynamic damage and die within a few hours. However, the cotyledons, stems, and growing points remain unaffected. Such plants usually recovered from the original photodynamic damage by producing new leaves and may require a second application. In this group the Type II response also depended on the age of the seedlings. For example, 6-day old soybean in which the primary leaves were still enclosed within the cotyledons were completely unaffected by the ALA+2,2'-DP treatment. On the other hand, 9-day old soybean plants, with expanded primary leaves, exhibited a typical Type II photodynamic herbicidal response. The only monitored monocot that exhibited this type of response was perennial blue grass in which about 30-40% of the sprayed leaves died; the plants subsequently recovered and developed new leaves.

The third type of photodynamic herbicidal response elicited by the ALA+2,2'-DP treatment is referred to as a type III response. Based on available data, monocots exhibited this type of response. Although the ALA+2,2'-DP treatment induced the accumulation of significant amounts of tetrapyrrole by the plants, the photodynamic damage was either imperceptible as in wheat, oat, and corn, or when noticeable as in barley, was confined to the upper half of a small proportion of the sprayed plants. In that case the photodynamic damage consisted of small necrotic regions. The seedlings continued to grow vigorously and developed into healthy plants.

The photodynamic formulations described in this example exhibited an excellent measure of species, age and organ-dependent selectivity. While dicotyledenous weeds such as lambsquarter, mustard, red root pigweed and common purselane were highly susceptible to the tetrapyrrole-induced photodynamic damage, monocots such as corn, wheat, oats, and barley were not adversely affected by the spray. Other dicots were either unaffected by the spray at an early stage of development as in soybean, or recovered fully from a rapid destruction of the primary leaves by producing new and healthy leaves, as was observed for kidney bean, soybean and cotton. Furthermore some tissues which accumulated tetrapyrroles such as bean stems did not exhibit any photodynamic damage. The biochemical basis of this organ, age and species-dependent photodynamic herbicidal selectivity appears to be dependent among other things on the rates of tetrapyrrole turnover and on a differential enhancement of the MV and DV tetrapyrrole biosynthetic pathways in any given plant species.

SECTION II

EXAMPLES OF DEFOLIATION AND FRUIT DROP

EXAMPLE 3

Defoliation Of "Red Delicious", "Golden Delicious", "Winesap" and "Prima" Apple Cultivars Under Greenhouse Conditions Scion wood of "Red Delicious", "Golden Delicious", "Winesap" and "Prima" apple cultivars was collected from the University of Illinois Pomology Research Farm. These were "whip and tongue" grafted onto seedling rootstock (purchased from Pacific Coast Nursery, Portland, Oreg.). Following grafting, seedlings were placed in plastic bags containing moist vermiculite, and kept in a cold room for two weeks at 1° C. to induce healing. The seedlings were then held in a cold chamber at 10° C. until needed.

Seedlings were later planted in 15 cm plastic pots containing a 1:1:1:1 (v/v/v/v) mixture of soil, vermiculite, peat, and sand media. These were grown in a greenhouse at 28° C. under a 14 h light—10 h dark photoperiod. Light intensity was supplied by three, 1000 W metal halide lamps. Light intensity was 24 W/m$^2$.

Following five days of growth at 23° C., the apple seedlings were treated as follows: (a) solvent only (control); (b) 20 mM ALA (Biosynth Int'l, Skokie, Ill.); (c) 30 m Methyl nicotinate (EN) (Aldrich Chem. Co., Milwaukee, Wis.); and (d) 20 mM of ALA plus 30 mM of EN. The solvent consisted of polyethylene glycol (Sigma Chem. Co., St. Louis, Mo.):methyl alcohol:-Tween 80:water at 7:2:1:90 (v/v/v/v) (Rebeiz, C. A., Montazer-Zouhoor, A., Mayasich, J. M., Tripathy, B. C., Wu, S., and Rebeiz, C. C., *CRC Crit. Rev. in Plant Sci.*, 6:385-435 (1988)). pH was adjusted to 3.5 to facilitate the penetration of ALA into the leaves. Solutions were delivered as a fine and uniform spray with a spray gun nozzle. The solutions were placed in a Binks Wren air brush, and the delivery of a fine mist (average diameter droplet size of 125 microns) was achieved by pumping the solution through metal tubing using compressed $CO_2$. One end of the tube was inserted into the gun intake hose, while the other end was dipped into the solution. Leaves were sprayed to a drip.

Treatment of the four apple cultivars was replicated three times in a randomized split plot design (four trees per replicate of each cultivar). After spraying, trees were transferred to a dark-growth chamber at 28° C. and kept from 6:00 p.m. to 9:00 a.m. the following morning in order to allow for the dark conversion of ALA to tetrapyrroles.

After 15 hours in darkness, plants were moved to the greenhouse for evaluation of growth and photodynamic damage over a period of 30 days. Plants were periodically photographed to record response to treatment. A Pentax Super program camera, equipped with an SMC Pentax-A 1:1.4, 50 mm lens, and a digital back recording the date and time of each shot on the prints obtained, was used. A 400 ASA Kodacolor film was used. First photographic records were taken before treatment and then at 1, 3, 8, 10, 17 and 30 days after exposure to light. Photodynamic damage consisted of the sum of tissue necrosis and leaf abscission.

A gram leaf sample (collected from both the top and the bottom of each of the seedlings) was homogenized in a Polytron homogenizer for one minute in 7 ml of acetone and 0.1N ammonium hydroxide (9:1, v/v). Acetone serves to extract the tetrapyrroles while ammonium hydroxide maintains the medium basic, thereby preventing loss of the Mg-atom from metalated tetrapyrroles. During homogenization, samples were handled under a green safelight which does not affect the tetrapyrrole content of the tissues.

After homogenization, extracts were centrifuged at 18,000 rpm for 12 min. at 1° C. to separate lipoproteins and cell debris from the supernatant containing tetrapyrroles. Chlorophyll and other fully esterified tetrapyrroles were removed by first extracting the supernatant with hexane followed by an equal volume of hexane and then with a 1/3 volume of hexane (Rebeiz, C. A., Mattheis, J. R., Smith, B. B., Rebeiz, C. C., and Dayton, D. F. *Arch. Biochem. Biophys.* 171:549-567 (1975)). Protoporphyrin IX (proto), Mg-protoporphyrin monoester (MPE), and protochlorophyllide (Pchlide) remained in the hexane-extracted acetone fraction (HEAF). The amount of tetrapyrroles in the HEAF was determined by spectrofluorometry.

Fluorescence emission and excitation spectra of the HEAF were recorded at room temperature (23.5° C.) and at 77° K. (frozen in liquid nitrogen) using a fully corrected photon counting spectrofluorometer (model SLM 8000 DS) equipped with two red-sensitive, extended S 20 photomultipliers (EMI 9658), and interfaced with an IBM Model 30 PC. Room temperature determinations were performed on 0.3 ml aliquots in a cylindrical micro-cell of 3 mm in diameter. Analytical techniques used for precise quantitative determination of the various tetrapyrroles are described by Rebeiz, C. A., Mattheis, J. R., Smith, B. B., Rebeiz, C. C., and Dayton, D. F., *Arch. Biochem. Biophys.* 171:549-567 (1975); Smith, B. B., and Rebeiz, C. A., *Photochem. Photobiol.* 26:527-532 (1977); Bazzaz, M. B., and Rebeiz, C. A., *Photochem. Photobiol.* 30:709 (1979); and Rebeiz, C. A., Danjell, H., and Mattheis, J. R., in *4th Symp. Biotechnol. Energy Prod. Conserv.* (Scot, C. D., Ed.) John Wiley & Sons, New York, 413-439 (1982). Recording of spectra and conversion of digital spectral data into concentrations were automatically performed by the microcomputer (Rebeiz, C. A., Danjell, H., and Mattheis, J. R., supra). For room temperature spectra, both the emission and the excitation band width were set at 4 nm. The photon count was integrated for 0.5 seconds at each 1 nm increment. Ratios of MV MPE to DV MPE and of MV pchlide to DV Pchlide were calculated from spectra recorded in ether at 77° K. (Tripathy, B. C., and Rebeiz, C. A., *Anal. Biochem.* 149:43-61 (1985)). The MV and DV tetrapyrrole content in a sample was determined from MV and DV tetrapyrrole ratios obtained at 77° K. and from total pigment content determined at room temperature.

Total protein was determined using the bicinchoninic acid (BCA) method Smith, P. K., Krohn, R. I., Hermanson, G. T., Mallia, A. K., Gardner, F. H., Provenzano, M. D., Fujimoto, E. K. Goeke, N. M., Olson, P. J. and Klenk, D. C., *Anal. Biochem.* 150:76-85 (1985), after resuspending the pellet obtained after centrifugation in distilled water. Absorbance was monitored on a Sequoia-Turner Model 340 spectrophotometer. Statistical analysis was conducted on an IBM P.C. Model 80, using a software package available from SAS Industries, Inc. Data were analyzed as a randomized split block design using the linear model. Testing for significant differences among cultivars and/or treatments was evaluated using the protected LSD test.

In general, leaves exhibited photodynamic injury in both ALA+EN and ALA treatments just a few hours after exposure to light. This was expressed in the form of wilting and necrosis of leaves. Complete defoliation of trees was achieved after 30 days following treatment (Table III).

TABLE III

| Percent Defoliation Of "Golden Delicious" Seedlings In The Greenhouse Over Time | | | | | | |
|---|---|---|---|---|---|---|
| Day: | 1 | 3 | 8 | 10 | 17 | 30 |
| Treatment | | | % Defoliation | | | |
| Control[1] | 0.77 | 2.12 | 2.00 | 5.00 | 6.19 | 6.19 |
| EN[2] | 1.13 | 1.55 | 3.39 | 3.39 | 4.08 | 4.08 |
| ALA[3] | 27.78 | 48.61 | 70.83 | 73.61 | 80.55 | 81.25 |
| ALA + EN[4] | 47.27 | 75.40 | 94.08 | 94.08 | 96.64 | 98.72 |

[1]Solvent only (polyethylene glycol:methyl alcohol:Tween 80:water at 7:2:1:90 (v/v/v/v)).
[2]30 mM ethyl nicotinate
[3]20 mM 5-aminolevulinic acid.
[4]20 mM 5-aminolevulinic acid + 30 mM ethyl nicotinate.

The experiments indicate that the detachment of the leaves from the stem is caused by the formation of an abscission layer at the leaf petiole level. The photodynamic phenomenology expressed by the various apple cultivars under greenhouse conditions is briefly described below.

For "Golden Delicious" seedlings, more than 75% of the leaves abscised by the third day following treatment with ALA+EN and defoliation was complete after 30 days (Table III). Except for some negligible browning, EN-treated and control plants exhibited no photodynamic damage (Table III).

"Red Delicious" seedlings lost 77% of their leaves 17 days after treatment with ALA+EN (Table IV). Therefore, the response of "Red Delicious" seedlings to ALA+EN treatment was slower than that observed for "Golden Delicious". Control and EN-treated "Red Delicious" seedlings did not exhibit any noticeable photodynamic damage (Table IV).

TABLE IV

Percent Defoliation Of "Red Delicious" Seedlings In The Greenhouse Over Time

| Day: | 1 | 3 | 8 | 10 | 17 | 30 |
|---|---|---|---|---|---|---|
| Treatment | | | % Defoliation | | | |
| Control[1] | 0.00 | 1.65 | 1.90 | 1.90 | 1.90 | 1.90 |
| EN[2] | 0.30 | 0.79 | 1.37 | 1.37 | 1.37 | 1.37 |
| ALA[3] | 27.15 | 41.03 | 55.30 | 56.69 | 59.47 | 60.86 |
| ALA + EN[4] | 21.47 | 29.70 | 50.11 | 54.06 | 77.14 | 88.83 |

[1]Solvent only (polyethylene glycol:methyl alcohol:Tween 80:water at 7:2:1:90 (v/v/v/v)).
[2]30 mM ethyl nicotinate
[3]20 mM 5-aminolevulinic acid.
[4]20 mM 5-aminolevulinic acid + 30 mM ethyl nicotinate.

The photodynamic phenomenology of "Winesap"-seedlings differed from the previous two cultivars. Overall, ALA treatment resulted in continuously higher percentage leaf drop over ALA+EN treatment (Table V). Almost 50% defoliation was achieved with ALA alone after the first day of treatment (Table V).

TABLE V

Percent Defoliation of "Winesap" Seedlings in The Greenhouse Over Time

| Day: | 1 | 3 | 8 | 10 | 17 | 30 |
|---|---|---|---|---|---|---|
| Treatment | | | % Defoliation | | | |
| Control[1] | 0.30 | 0.58 | 1.17 | 1.17 | 1.17 | 1.17 |
| EN[2] | 0.89 | 1.62 | 2.13 | 2.13 | 2.62 | 2.62 |
| ALA[3] | 49.84 | 62.74 | 73.44 | 76.71 | 76.71 | 80.97 |
| ALA + EN[4] | 35.03 | 45.86 | 65.27 | 65.27 | 70.15 | 73.71 |

[1]Solvent only (polyethylene glycol:methyl alcohol:Tween 80:water at 7:2:1:90 (v/v/v/v)).
[2]30 mM ethyl nicotinate
[3]20 mM 5-aminolevulinic acid.
[4]20 mM 5-aminolevulinic acid + 30 mM ethyl nicotinate.

TABLE VI

Percent Defoliation Of "Prima" Seedlings in The Greenhouse Over Time

| Day: | 1 | 3 | 8 | 10 | 17 | 30 |
|---|---|---|---|---|---|---|
| Treatment | | | % Defoliation | | | |
| Control[1] | 0.79 | 1.98 | 2.53 | 2.53 | 2.53 | 2.53 |
| EN[2] | 0.79 | 1.19 | 1.58 | 1.58 | 1.58 | 1.58 |
| ALA[3] | 37.50 | 52.78 | 66.67 | 66.67 | 73.61 | 74.31 |
| ALA + EN[4] | 34.65 | 57.12 | 61.95 | 67.22 | 75.92 | 78.48 |

[1]Solvent only (polyethylene glycol:methyl alcohol:Tween 80:water at 7:2:1:90 (v/v/v/v)).
[2]30 mM ethyl nicotinate
[3]20 mM 5-aminolevulinic acid.
[4]20 mM 5-aminolevulinic acid + 30 mM ethyl nicotinate.

Again, control and EN treatments exhibited negligible damage (Table VI).

In general, the four apple cultivars exhibited a similar response to treatment with ALA and EN. Indeed, no significant differences among cultivars were observed in protoporhyrin IX (Proto), MV Mg-protoporphyrin monoester (MV MPE), DV Mg-protoporphyrin monoester (DV MPE), MV Protochlorophyllide (MV Pchlide), and DV Protochlorophyllide (DV Pchlide) accumulation in leaves in all treatments (Tables VII-XI).

TABLE VII

Leaf Accumulation Of Protoporphyrin IX In Each Of The Four Cultivars Following Treatment

| | Protoporphyrin IX accumulation in nmoles/100 mg protein | | | |
|---|---|---|---|---|
| Cultivar | Control[1] | EN[2] | ALA[3] | ALA + EN[4] |
| Golden Delicious | 3.16 A[Y] | 7.63 A | 15.83 A | 36.47 B |
| Prima | 6.38 A | 9.62 A | 20.07 A | 9.66 A |
| Red Delicious | 5.96 A | 5.43 A | 15.22 AB | 22.89 B |
| Winesap | 4.24 A | 7.41 A | 24.17 B | 25.83 B |

[Y]Mean separation for various treatment within a cultivar by LSD at the 5% level of significance. Means followed by the same letter within a cultivar are not significantly different.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

TABLE VIII

Leaf Accumulation of Monovinyl Mg-protoporphyrin In Monoester Each Of The Four Cultivars Following Treatment

| | MV MPE accumulation in nmoles/100 mg protein | | | |
|---|---|---|---|---|
| Cultivar | Control[1] | EN[2] | ALA[3] | ALA + EN[4] |
| Golden Delicious | 2.32 A[Y] | 3.82 A | 1.04 A | 5.81 A |
| Prima | 2.81 A | 4.53 AB | 12.11 B | 1.44 A |
| Red Delicious | 2.71 A | 2.48 A | 1.70 A | 2.27 A |
| Winesap | 2.86 A | 3.18 A | 0.75 A | 0.98 A |

[Y]Mean separation for various treatment within a cultivar by LSD at the 5% level of significance. Means followed by the same letter within a cultivar are not significantly different.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

TABLE IX

Leaf Accumulation Of Divinyl Mg-protoporphyrin Monoester In Each Of The Four Cultivars Following Treatment

| | DV MPE accumulation in nmoles/100 mg protein | | | |
|---|---|---|---|---|
| Cultivar | Control[1] | EN[2] | ALA[3] | ALA + EN[4] |
| Golden Delicious | 2.57 A[Y] | 3.55 A | 40.17 B | 56.07 B |
| Prima | 4.78 A | 4.53 A | 53.64 B | 46.33 B |
| Red Delicious | 2.74 A | 2.57 A | 45.20 B | 102.58 C |
| Winesap | 3.03 A | 4.44 A | 53.76 B | 73.34 B |

[Y]Mean separation for various treatment within a cultivar by LSD at the 5% level of significance. Means followed by the same letter within a cultivar are not significantly different.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

TABLE X

Leaf Accumulation Of Monovinyl Protochlorophyllide In Each Of The Four Cultivars Following Treatment

| | MV Protochlorophyllide accumulation in nmoles/100 mg protein | | | |
|---|---|---|---|---|
| Cultivar | Control[1] | EN[2] | ALA[3] | ALA + EN[4] |
| Golden Delicious | 17.71 A[Y] | 7.37 A | 144.56 B | 220.79 B |
| Prima | 20.03 A | 8.32 A | 257.74 B | 206.82 B |
| Red Delicious | 9.40 A | 6.24 A | 176.53 B | 403.45 C |
| Winesap | 23.64 A | 14.12 A | 180.20 B | 302.56 C |

[Y]Mean separation for various treatment within a cultivar by LSD at the 5% level of significance. Means followed by the same letter within a cultivar are not significantly different.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

TABLE XI

Leaf Accumulation Of Divinyl Protochlorophyllide
In Each Of The Four Cultivars Following Treatment

| Cultivar | DV Protochlorophyllide accumulation in nmoles/100 mg protein | | | |
|---|---|---|---|---|
| | Control[1] | EN[2] | ALA[3] | ALA + EN[4] |
| Golden Delicious | 0.59 A[Y] | 0.75 A | 2.84 A | 6.13 A |
| Prima | 1.24 A | 0.63 A | 2.07 A | 4.95 A |
| Red Delicious | 0.62 A | 0.24 A | 1.74 A | 1.13 A |
| Winesap | 0.84 A | 0.58 A | 51.97 B | 8.91 A |

[Y]Mean separation for various treatment within a cultivar by LSD at the 5% level of significance. Means followed by the same letter treatments within a cultivar are not significantly different.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

However, significant differences among treatments were observed for proto, IX, DV MPE, and MV Pchlide accumulations (Tables VII-XI). A significant cultivar x treatment interaction was obtained only in MV Pchlide accumulation. As for percent leaf defoliation, no significant differences were observed among cultivars. Significant differences were, however, observed among treatments along with a significant cultivar x treatment interaction (Table XII).

TABLE XII

Percent Leaf Defoliation Of Four Apple Cultivars

| Cultivar | % Leaf Defoliation | | | |
|---|---|---|---|---|
| | Control[1] | EN[2] | ALA[3] | ALA + EN[4] |
| Golden Delicious | 6.19 A[Y] | 4.08 A | 81.50 B | 98.72 B |
| Prima | 2.53 A | 1.58 A | 74.31 B | 78.48 B |
| Red Delicious | 1.90 A | 1.36 A | 60.86 B | 88.83 B |
| Winesap | 1.17 A | 2.62 A | 80.97 B | 73.71 B |

[Y]Mean separation for various treatment within a cultivar by LSD at the 5% level of significance. Means followed by the same letter treatments within a cultivar are not significantly different.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

Overall, accumulation of proto and extent of leaf defoliation for the cultivars were not significantly different between ALA+EN and ALA; however, they were both significantly higher than EN and control treatments (Table XIII).

The accumulation of DV MPE and NV Pchlide was significantly higher in ALA+EN treated seedlings than in the other three treatments (Table XIII). However, ALA treated trees also exhibited significantly higher DV MPE and MV Pchlide accumulation in leaves than EN-treated and control plants. The EN treated seedlings and the controls were not significantly different (Table XIII).

Since the control and the EN treated seedlings did not accumulate significant amounts of proto, MVMPE, DV MPE, MV Pchlide, and DV Pchlide, and since almost no defoliation was observed in all four cultivars, it can be stated that the exogenous ALA and ALA+EN applications were definitely responsible for the accumulation of tetrapyrroles and for the successful defoliation of apple trees. When applied with ALA, EN significantly increased the dark conversion of exogenous ALA to both DV MPE and MV Pchlide, beyond the level obtained by ALA alone (Table XIII). Therefore, EN can be classified as an enhancer of ALA conversion to MV Protochlorophyllide and to DV MPE.

ALA+EN treatment induced a significantly higher proto accumulation in "Golden Delicious" than in the other treatments. However, ALA+EN treated "Golden Delicious" seedlings did not accumulate higher levels of proto than ALA treated seedlings in other cultivars. Furthermore, in "Winesap", ALA treatment resulted in a significantly higher level of Proto accumulation than that of the Control or EN treatments (Table VII).

ALA-treated seedlings of "Prima" exhibited a higher MVMPE accumulation than ALA+EN treated plants. However, no significant differences in MV MPE accumulation were exhibited among any of the treatments of "Golden Delicious", "Red Delicious", and "Winesap" cultivars (Table VIII).

"Golden Delicious", "Prima", and "Winesap" cultivars did not exhibit any significant differences in DV MPE accumulation between the ALA and ALA+EN treated plants. However, ALA+EN treated 'Red Delicious' trees exhibited a significantly higher DV MPE accumulation than ALA treated plants (Table IX).

"Red Delicious" and "Winesap" ALA-treated trees exhibited a significantly higher MV Pchlide accumulation than ALA+EN-treated trees. The other two cultivars did not exhibit a significant difference between ALA and ALA +EN treatments (Table X).

TABLE XIII

Mean Accumulation Of Tetrapyrroles in nmoles/100 mg Protein In "Red Delicious", "Winesap", "Golden Delicious" And "Prima" Cultivars And The Percent Defoliation For The Four Treatments

| Treatment | Proto[1] | MV MPE[2] | DV MPE[3] | MV Pide[4] | DV Pide[5] | % Defol[6] |
|---|---|---|---|---|---|---|
| | | | nmoles/100 mg protein | | | |
| Control[7] | 4.94 B[Y] | 2.68 A | 3.28 C | 17.70 C | 0.82 A | 2.95 B |
| EN[8] | 7.52 B | 3.50 A | 3.77 C | 9.01 C | 0.55 A | 2.41 B |
| ALA[9] | 18.82 A | 3.90 A | 48.19 B | 189.76 B | 14.65 A | 74.41 A |
| ALA + EN | 23.71 A | 2.62 A | 69.58 A | 283.40 A | 5.28 A | 84.93 A |
| Signif.[Z] | * | NS | * | * | NS | * |

[Z]Non-significant (NS), significant at the 5% level (*).
[Y]Mean separation within columns by LSD at the 5% level of significance. Means followed by the same letter for various treatments within a tetrapyrrole accumulation are not significantly different.
[1]Protoporphyrin IX.
[2]Monovinyl Mg-protoporphyrin monoester.
[3]Divinyl Mg-protoporphyrin monoester.
[4]Monovinyl protochlorophyllide.
[5]Divinyl protochlorophyllide.
[6]Percent defoliation.
[7]Solvent only (polyethylene glycol:methyl alcohol:Tween 80:water at 7:2:1:90 (v/v/v/v)).
[8]Ethyl nicotinate.
[9]5-aminolevulinic acid.

Only ALA-treated "Winesap" trees exhibited a significant difference in their DV Pchlide accumulation when compared to the other three treatments (Table XI).

For all four cultivars, there was no significant difference in defoliation between ALA and ALA+EN treated plants (Table XIII).

Figure 3:
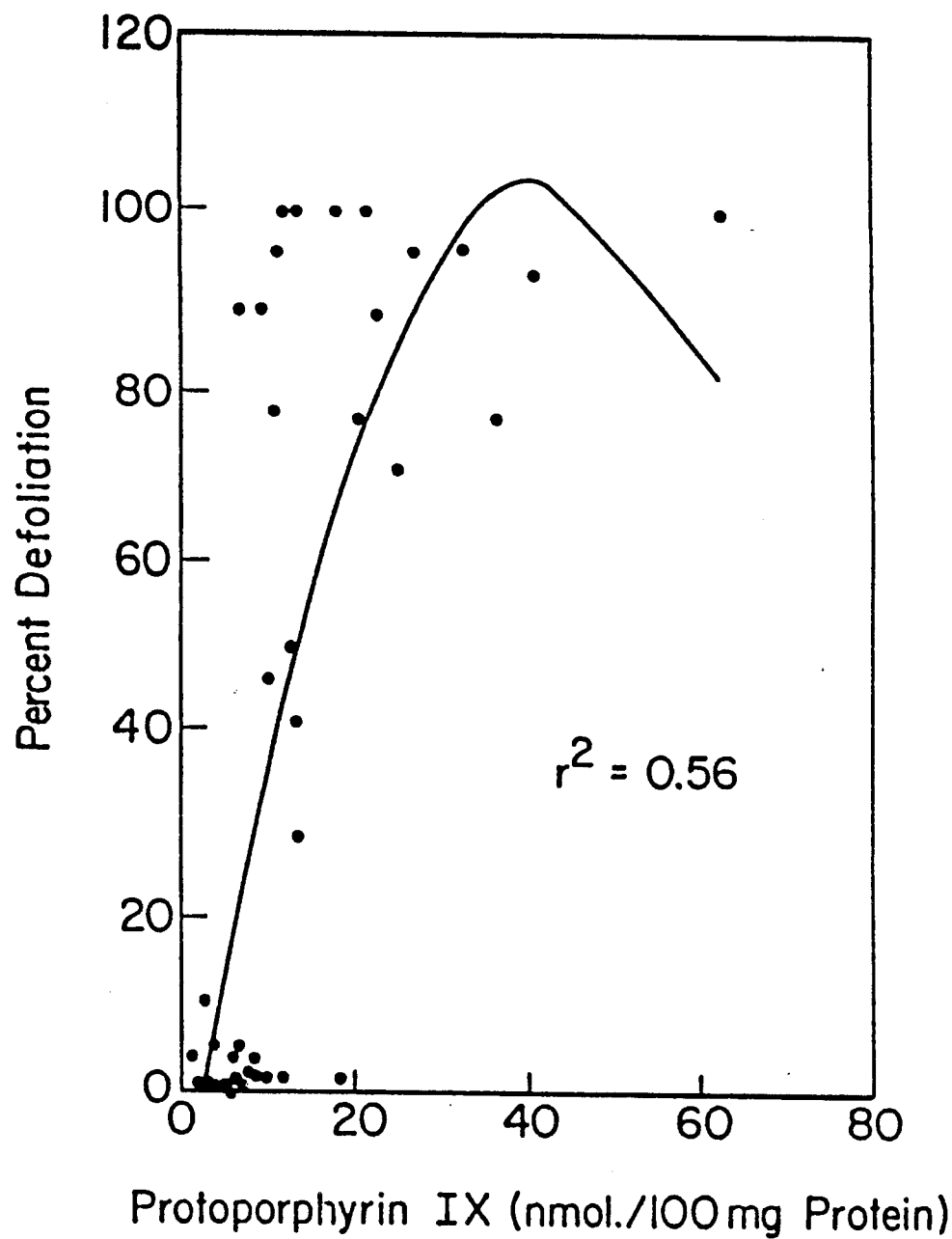
FIG. 3 depicts the percent defoliation of apple seedlings as related to the accumulation of protoporphyrin IX (*coefficient of determination ($r^2$) is significant at the 5% level)
Figure 4:
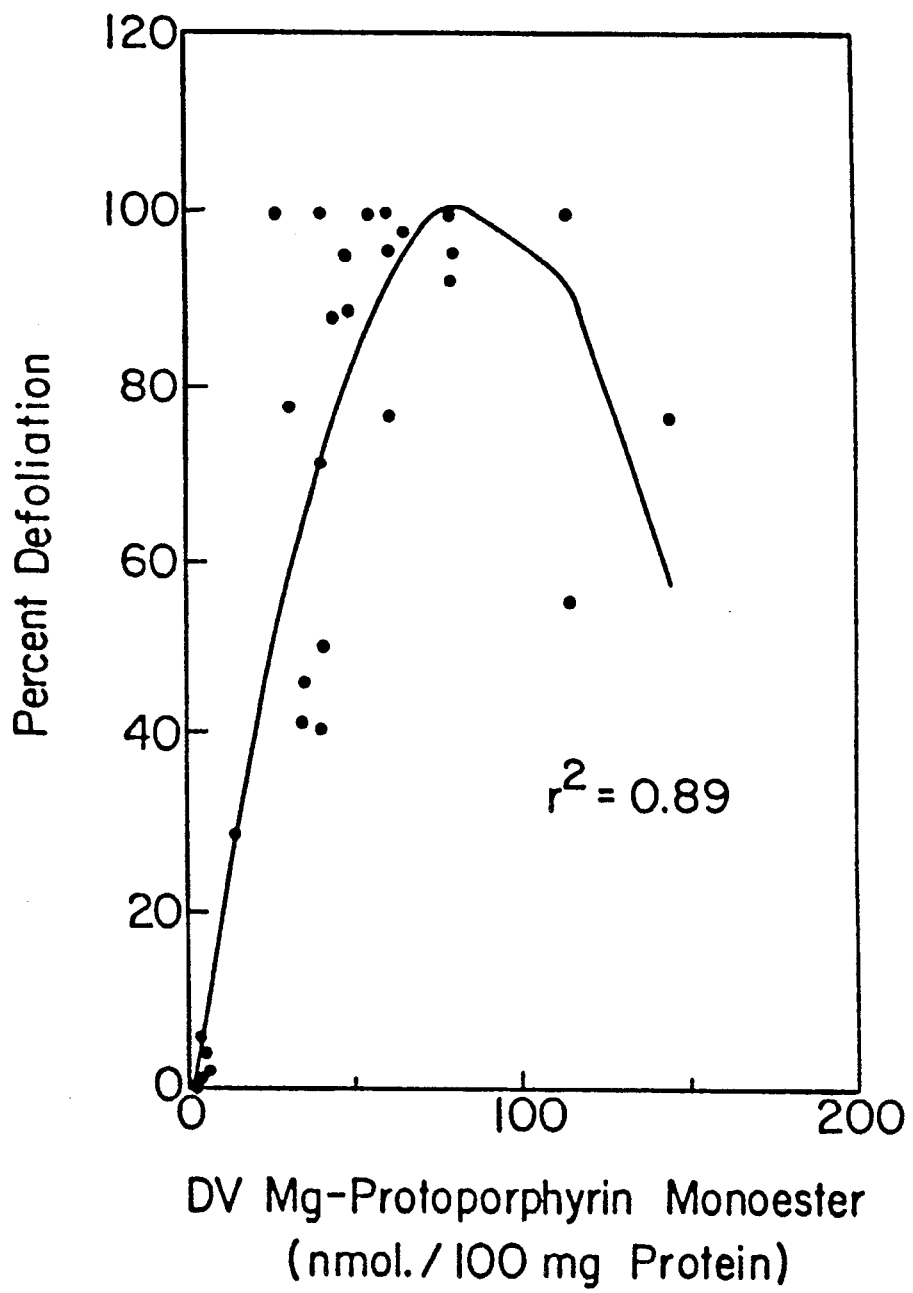
FIG. 4 depicts the percent defoliation of apple seedlings as related to the accumulation of divinyl Mg protoporphyrin monoester (*coefficient of determination ($r^2$) is significant at the 5% level)
Figure 5:
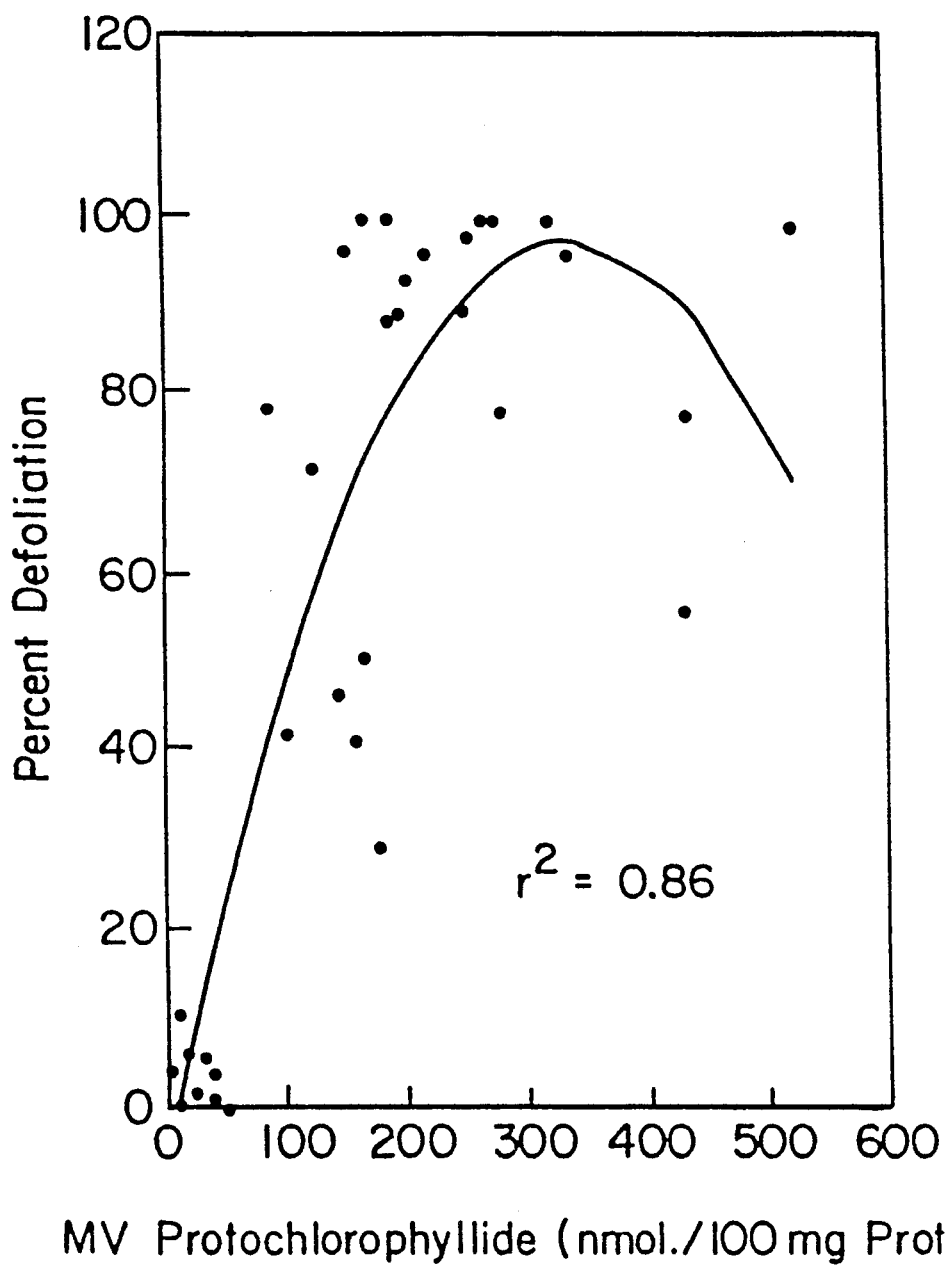
FIG. 5 depicts the percent defoliation of apple seedlings as related to the accumulation of monovinyl protochlorophyllide (*coefficient of determination ($r^2$) is significant at the 5% level).

Proto, DV MPE, and MV Pchlide accumulation in leaves of the various cultivars were positively correlated to leaf defoliation (FIGS. 3, 4 and 5). In other words, the higher accumulation of proto, DV MPE, and MV Pchlide, resulted in an increased rate of defoliation. It was observed, however, that beyond a certain tetrapyrrole concentration level, accumulation of proto, DV MPE and MV Pchlide inhibited defoliation (FIGS. 3, 4 and 5).

Because treated seedlings were not held in cold storage, and because of the favorable environmental conditions in the greenhouse, defoliated seedlings exhibited healthy, green regrowth. This in turn indicates that shoots and buds were not damaged as a result of these treatments. Interestingly, more regrowth was observed with plants sprayed with ALA+EN than with those sprayed with ALA alone. In other words, in addition to enhanced tetrapyrrole accumulation, the addition of EN to ALA appeared to exert growth promoting effects on the defoliated shoots.

Comparison of ALA+EN With Known Chemical Defoliants

Knight's (Knight, J. N., *J. Hort. Sci.* 58(4):471–476 (1983)) results from use of FeEDTA and CuEDTA on "Cos's Orange Pippin" apple trees were comparable to results obtained with the composition according to the invention. Three percent FeEDTA and 2.1% CuEDTA resulted in 81 and 89% defoliation, respectively, of "Cox's Orange Pippin" apple trees 40 days following treatment (Knight, J. N. supra), whereas the composition of ALA+EN according to the invention resulted in nearly 99% and 89% defoliation of "Golden Delicious" and "Red Delicious", respectively, 30 days following treatment (Table XII). ALA+EN-treated "Prima" trees were 78.5% defoliated compared to 74% defoliation of "Winesap" trees (Table XII).

Larsen's (Larsen, F. E., *Proc. Internt. Plant Prop. Soc.* 17:157-172 (1967)) use of 1% S,S,S,-tributylphosphoromtrithionate (DEF) resulted in a complete defoliation of "Winesap" four weeks following treatment and in 80% defoliation of "Rome Beauty" three weeks following treatment. However, DEF did not bring about defoliation of "Red King" apple seedlings (Larsen, F. E., supra). Some excessive damage was reported on the trees as compared to non-noticeable damage on trees sprayed in accordance with the invention. Healthy regrowth followed spraying when trees were kept under favorable environmental conditions.

Defoliation of "Golden Delicious" with Ethrel ® at varying concentrations was significantly inferior to defoliation with the composition according to the invention because only 26% leaf drop was obtained (Jones, D. L., Nichols, D. G., Thompson, W. K., and Jager, L. A., *Australian Journal of Experimental Agriculture and Animal Husbandry* 13:460-464 (1973)). In another study by Larsen, 8,000 ppm Ethrel resulted in 95% defoliation of "Red Delicious" nursery trees 3-4 weeks following application (Larsen, F. E., *J. Amer. Soc. Hort. Sci.* 95:662-663 (1970)).

EXAMPLE 4

Defoliation And Fruit Drop of "Red Delicious" and "Golden Delicious" Apple Cultivars Under Field Conditions A total of sixteen apple trees growing at the Pomology Research Farm in Urbana and representing two cultivars, namely "Red Delicious" and "Golden Delicious" were subjected to four different treatments. Each treatment was applied to two individual trees. Three branches, 36 inches in length were selected from each tree for treatment. Therefore, each of the four treatments was sprayed on a total of six branches. Fruits were counted on each branch before spraying.

The four treatments consisted of the following:
(a) control which consisted of solvent only (polyethylene glycol:Methyl alcohol:Tween 80:water at 7:2:1:90 (v/v/v/v));
(b) 40 mM ALA; and
(c) 30 mM EN; (d) 40 mM ALA+30 mM EN.

Handling of solutions and sprays was similar to that described in Example 3. Trees of "Red Delicious" were sprayed on 9/15/88 starting at 2 p.m. and terminating at 6 p.m. It is important to note that a heavy rainfall occurred in the following morning. Trees of "Golden Delicious" were sprayed on Sep. 16, 1988 starting at 2 p.m. and ending at 6 p.m. No rain showers followed this set of treatments.

To evaluate the degree of photodynamic damage and extent of fruit drop, treated branches were photographed before spraying and on the 10th day after spraying for "Golden Delicious" and on the 11th day after spraying for the "Red Delicious". Photographic recording was conducted as described earlier, except that a 28-135 mm zoom lens was used. Number of fruit drop was recorded every day or every other day and percent fruit drop was calculated. Data were analyzed in a randomized complete block design.

Treatment of "Red Delicious" branches resulted in neither significant defoliation nor in fruit abscission (Table XIV), and treated fruits did not exhibit skin injury. Because "Golden Delicious" and "Red Delicious" responded more or less in the same manner to the application of ALA and ALA+EN under greenhouse conditions as shown in Example 3, and because both belong to the same DMV/LDV greening group, the observed difference in the field between the two cultivars is probably not due to differences in their susceptibility to ALA and ALA+EN treatments, but rather due to the heavy rain that fell the morning after having sprayed the "Red Delicious" trees.

"Golden Delicious" trees treated with ALA or with ALA+EN underwent a 100% defoliation by the 13th day after spraying. By that time, fruit drop was also 100% (Table XIV). Visual examination of abscised fruits revealed the formation of a pronounced abscission layer at the base of the pedicel and some fruits exhibited pronounced skin browning. Branches sprayed with EN and solvent only (i.e., control) remained healthy and did not exhibit a significant level of defoliation or fruit abscission beyond normal levels. No injury was observed on sprayed fruit.

Significantly higher leaf defoliation and fruit abscission were observed in ALA and ALA+EN treatments when compared to the control and EN treated branches (Table XIV). This was not so in the case of the "Red Delicious" cultivar where no significant difference between treatments was observed (Table XIV).

TABLE XIV

Percent Fruit Drop Of "Red Delicious" and "Golden Delicious" Cultivars Following Spray Treatments

| Treatment | % Fruit Drop | |
|---|---|---|
| | Golden Delicious | Red Delicious |
| Control[1] | 41.67 b[x]A[y] | 27.94 aA |
| EthylNicotinate[2] | 26.27 bA | 44.69 aA |
| ALA[3] | 100.00 aA | 41.19 aB |
| ALA + EN | [4]100.00 aA | 30.15 aB |

[x]Mean separation within cultivars by protected LSD at the 1% level of significance.
[y]Mean separation within treatments by protected LSD at the 1% level of significance.
[1]Solvent only (polyethylene glycol:methyl alcohol:Tween 80:water at 7:2:1:90 (v/v/v/v)).
[2]30 mM ethyl nicotinate.
[3]20 mM 5-aminolevulinic acid.
[4]20 mM 5-aminolevulinic acid + 30 mM ethyl nicotinate.

Comparison With Other Known Chemical Fruit Harvesters

In other studies (Hartmann, H. T., Fadl, F., and Whisher, *J. Calif. Agric.* 21(7):5-7 (1967); Unrath, C. R. *J. Amer. Soc. Hort. Sci.* 94:387-391 (1967); Wilson, W. C., and Hendershott, C. H. *Proc. Amer. Soc. Hort. Sci.* 90:123-129 (1967)), chemicals were used to reduce the force separating the pedicel to facilitate mechanical harvesting. Therefore, the results from those studies are not comparable to those obtained in accordance with the invention where 100% defoliation and fruit drop were achieved following treatment of "Golden Delicious" trees (Table XXIX) without mechanical harvesting.

EXAMPLE 5

Defoliation of Tomato Under Greenhouse Conditions
A. MATERIALS AND METHODS

Seedlings of tomato, a DMV/LDV plant species, were grown in a greenhouse under a fourteen hour lightten hour dark photoperiod in vermiculite for twenty five days before spraying. (Tomato is accepted in the art as a model for potato). Two days before spraying, the aging cotyledons were removed and the seedlings with old and young developing leaves were sprayed in the afternoon in the greenhouse with 20 mM ALA (about 500 g/acre)+15 mM modulator (about 375 g/acre) at a rate of 40 gpa and an average droplet size of 75 μm. Eleven different modulators, the identities of which are shown in Table XXX, were tested. Studies on the mode of action of these modulators on cucumber revealed that the modulators acted as enhancers of the conversion of ALA to protochlorophyllide in cucumber. Depending on the solubility of the particular modulator, ALA and the modulator were dissolved either in a solvent made up of polyethylene glycol:methanol:-Tween 80:water (7:2:1:90 v/v/v/v) at a pH of 3.5 or in a solvent made up of polyethylene glycol: Tween 80:ethanol:methanol:water (7:1:45:45:2 v/v/v/v/v) at a pH of 3.5.

The plants were evaluated visually for growth and photodynamic damage over a period of ten days. The plants were periodically photographed to record response to treatment as described in the previous examples. The results of the treatment are shown in Table XV.

TABLE XV

Defoliation/Desiccation Of Tomato Seedlings By ALA and Nicotinic Acid Or Nicotinamide Modulators

| | | % Defoliation/desiccation | | | |
|---|---|---|---|---|---|
| | | Older Leaves | | Younger Leaves | |
| ALA | Modulator | Days After Treatment | | | |
| (20 mM) | (15 mM) | 2 | 7 | 2 | 7 |
| + | 6-aminonicotinamide | 100 | 100 | 85 | 85 |
| + | ethyl nicotinate | 95 | 95 | 91 | 91 |
| + | 2-hydroxynicotinic acid | 95 | 95 | 90 | 90 |
| + | 2-hydroxy-6-methyl pyridine-3-carboxylic acid | 95 | 95 | 74 | 74 |
| + | ethyl 2-methyl nicotinate | 95 | 95 | 71 | 71 |
| + | N-methylnicotinamide | 90 | 90 | 93 | 93 |
| + | N-benzyl-N-nicotinoyl nicotinamide | 90 | 90 | 67 | 65 |
| + | 4-hydroxy-7-trifluoro methyl-3-quinoline carboxylicacid | 90 | 90 | 85 | 85 |
| + | 4-hydroxy-7-methyl-1,8-naphthyridine-3-carboxylicacid | 89 | 89 | 95 | 95 |
| + | diethyl 3,4-pyridine dicarboxylate | 85 | 85 | 72 | 72 |
| + | niflumic acid | 82 | 82 | 73 | 73 |

An examination of Table XV reveals that tomato leaves were susceptible to combinations of ALA and nicotinic acid or nicotinamide modulators. Young developing leaves were less susceptible to treatment than the older, more mature leaves. Overall, ten modulators exhibited 88-90% or better defoliation of old leaves. Four of these modulators also exhibited 90% or better defoliation of young developing leaves.

EXAMPLE 6

Defoliation Of Cotton Under Greenhouse Conditions

Twenty four day-old vermiculite-grown cotton seedlings were used. Two days before spraying, aging cotyledons were excised and well-developed primary leaves (old leaves) as well as developing secondary leaves (young leaves) were treated by spraying with a combination of ALA and a given modulator. The identities of the modulators tested are set forth in Table XVI. ALA and modulator concentrations were 20 and 15 mM, respectively. Spraying and evaluation of photodynamic defoliation was exactly as described in Example 5.

The results of the tests are reported in Table XVI.

TABLE XVI

Defoliation/Desiccation of Cotton By ALA And Various Modulators

| MODULATOR[1] | % DEATH | | | |
|---|---|---|---|---|
| | YL[2]T[3]D2[4] | T OL[5]D2 | YL T D7[4] | T OL D7 |
| benzyl viologen dichloride monohydrate | 87 | 75 | 111[6] | 111 |
| di 2-pyridyl ketoneoxime | 69 | 81 | 111 | 111 |
| 2,2'-dithiobis(pyridine n-oxide) | 100 | 100 | 111 | 111 |
| 6,6'-dithiodinicotinic acid | 25 | 69 | 111 | 111 |
| methyl5-(benzloxycarbonyl)-2,4-dimethyl-3- | 50 | 57 | 111 | 111 |

TABLE XVI-continued
Defoliation/Desiccation of Cotton By ALA And Various Modulators

| MODULATOR[1] | % DEATH | | | |
|---|---|---|---|---|
| | YL[2]T[3]D2[4] | T OL[5]D2 | YL T D7[4] | T OL D7 |
| 1-methyl-2-pyrrole carboxaldehyde | 25 | 37 | 111 | 111 |
| 1-methyl-2-pyrrole carboxylic acid | 31 | 62 | 111 | 111 |
| pyrrole-2-carboxaldehyde | 25 | 87 | 111 | 111 |
| pyrrole [1,2-a]quinoxaline | 56 | 100 | 111 | 111 |
| phenyl 2-pyridyl ketoxime | 79 | 81 | 111 | 111 |
| 5-chloro-1,10-phenanthroline | 100 | 100 | 100 | 100 |
| dimidium bromide | 75 | 94 | 100 | 100 |
| 2,2'-dipyridyl | 100 | 100 | 100 | 100 |
| ethidium bromide | 87 | 75 | 100 | 100 |
| methyl viologen dichloride iodide | 100 | 100 | 100 | 100 |
| 1,10-phenanthroline | 100 | 100 | 100 | 100 |
| 4'-methyl-1,10-phenanthroline | 100 | 100 | 100 | 100 |
| 1-(carboxymethyl)pyridinium chloride | 94 | 100 | 94 | 100 |
| 1,1'-diethyl-4,4'-cyanine iodide | 87 | 100 | 94 | 100 |
| 4,4'-dimethyl-2,2'-dipyridyl | 94 | 100 | 94 | 100 |
| 1-dodecylpyridinium chloride monohydrate | 81 | 100 | 94 | 100 |
| 1,1'-diethyl-2,2'-cyanine iodide | 87 | 100 | 87 | 100 |
| 1,1'-diethyl-2,4'-cyanine iodide | 87 | 100 | 87 | 100 |
| 4,7-dimethyl-1,10-phenanthroline | 87 | 100 | 87 | 100 |
| 5,6-dimethyl-1,10-phenanthroline | 87 | 100 | 87 | 100 |
| 5-methyl-1,10-phenanthroline | 87 | 100 | 87 | 100 |
| 2,2':6'6''-terpyridine | 87 | 100 | 87 | 100 |
| 3,4,7,8-tetramethyl-1,10-phenanthroline | 87 | 100 | 87 | 100 |
| 6-amino nicotinamide | 85 | 100 | 85 | 100 |
| berberine hydrochloride hydrate | 62 | 100 | 75 | 100 |
| 5-phenyl-2-(4-pyridyl)oxazole | 75 | 100 | 75 | 100 |
| tert-butyl 4-acetyl3,5-dimethyl1-2-pyrrolecarcoxylate | 71 | 100 | 71 | 100 |
| 2-[4-(dimethylamino)styryl]-1-methyl pyridinium iodide | 71 | 100 | 71 | 100 |
| sanguinarine chloride | 71 | 100 | 71 | 100 |
| 1-furfurylpyrrole | 69 | 100 | 69 | 100 |
| 2,4,6-collidine p-toluene sulfonate | 62 | 100 | 62 | 100 |
| 3-ethyl-2-methyl-4,5,6,7-tetrahydroindol-4-one | 62 | 100 | 62 | 100 |
| 3-amino-2,6-di-methoxypyridine monohydrochloride | 50 | 100 | 50 | 100 |
| 5-amino-2-methoxy pyridine | 50 | 100 | 50 | 100 |
| 1-ethyl-3-OH-pyridinium bormide | 44 | 100 | 44 | 100 |
| 6-amino nicotinamide | 37 | 100 | 37 | 100 |
| ethyl 2-methyl nicotinate | 37 | 100 | 37 | 100 |
| ethyl nicotinate | 37 | 100 | 37 | 100 |
| 2-hydroxy-6-methyl pyridine-3-carboxylic acid | 37 | 100 | 37 | 100 |
| 2-hydroxynicotinic acid | 25 | 100 | 25 | 100 |
| niflumic acid | 25 | 100 | 25 | 100 |
| dibucaine hydrochloride | 14 | 100 | 14 | 100 |
| diethyl 3,4-pyridine dicarboxylate | 12 | 100 | 12 | 100 |
| ethyl nicotinate | 91 | 95 | 91 | 95 |
| 2-hydroxy nicotinic acid | 90 | 95 | 90 | 95 |
| 2-hydroxy-6-methyl pyridine-3-carboxylic acid | 74 | 95 | 74 | 95 |
| ethyl 2-methylnicotinate | 71 | 95 | 71 | 95 |
| 5-nitro-1,10-phenanthroline | 100 | 94 | 100 | 94 |
| phenanthridine | 81 | 94 | 81 | 94 |
| ethyl 3,5-dimethyl-2-pyrrolecarboxylate | 75 | 94 | 75 | 94 |
| 2-[4-(dimethylamino)styryl]-1-ethyl pyridinium iodide | 62 | 87 | 75 | 94 |
| isocarbostyril | 75 | 94 | 75 | 94 |
| 2,3-dihydroxypyridine | 62 | 94 | 62 | 94 |
| 2-chloro-6-methoxypyridine | 50 | 94 | 50 | 94 |
| 4-hydroxy-7-trifluoro methyl-3-quinoline carboxylic | 50 | 94 | 50 | 94 |
| 1-(dimethylamino)pyrrole | 44 | 94 | 44 | 94 |
| 4-hydroxy-7-methyl-1,8-naphthridine-3-carboxylic acid | 43 | 93 | 43 | 93 |
| N-methylnicotinamide | 93 | 90 | 93 | 90 |
| 4-hydroxy-7-trifluoro methyl-3-quinoline carboxylic | 85 | 90 | 85 | 90 |
| N-benzyl-N-nicotinoylnicotinateamide | 65 | 90 | 65 | 90 |
| 4-hydroxy-7-methyl-1,8-naphthridine-3-carboxylic acid | 95 | 89 | 95 | 89 |
| citrazinic acid | 81 | 87 | 81 | 87 |
| propidium iodide hydrate | 75 | 87 | 75 | 87 |
| 2-hydroxy-4-methyl quinoline | 71 | 87 | 71 | 87 |
| 3-cyano-4,6-dimethyl-2-hydrochloride | 62 | 87 | 69 | 87 |
| N-benzyl-N-nicotinoyl nicotinatemide | 56 | 87 | 56 | 87 |
| diethyl-2,4-dimethyl pyrrole-3,5-dicarboxylate | 56 | 87 | 56 | 87 |
| 4-(dimethylamino)pyridinium bromide perbromide | 56 | 87 | 56 | 87 |
| 1-(2-cyanoethyl)pyrrole | 37 | 81 | 50 | 87 |
| N-methylnicotinamide | 25 | 87 | 25 | 87 |
| diethyl3,4-pyridine dicarboxylate | 72 | 85 | 72 | 85 |
| niflumic acid | 73 | 82 | 73 | 82 |
| 4,7-diphenyl-1,10-phenanthroline | 75 | 81 | 75 | 81 |
| 8-hydroxy-5-nitroquinoline | 75 | 81 | 75 | 81 |
| 5,7-dichloro-8-hydroxyquinoline | 81 | 75 | 81 | 75 |

TABLE XVI-continued

Defoliation/Desiccation of Cotton By ALA And Various Modulators

| MODULATOR[1] | % DEATH | | | |
|---|---|---|---|---|
| | YL[2]T[3]D2[4] | T OL[5]D2 | YL T D7[4] | T OL D7 |
| 2,6-dimethoxypyridine | 50 | 75 | 50 | 75 |
| 5-chloro-8-hydroxy-7-iodoquinoline | 44 | 69 | 44 | 75 |
| 5,7-dibromo-8-hydroxyquinoline | 44 | 75 | 44 | 75 |
| bis-N-methyl acridinium nitrate | 31 | 75 | 31 | 75 |
| 2,9-dimethyl-4,7-phenyl-1,10-phenanthroline | 25 | 25 | 25 | 25 |
| 3-hydroxypicolinic acid | 12 | 19 | 19 | 19 |
| 1-isoquinolinecarboxylic acid | 12 | 12 | 12 | 12 |
| picolinic acid | 12 | 12 | 12 | 12 |

[1]ALA and modulator concentrations were 20 and 15 mM respectively.
[2]YL = young leaves.
[3]T = treated.
[4]D2, D7 = damage 2 and 7 days after spraying.
[5]OL = old leaves.
[6]The number 111 in each column refers to the development of nutrition deficiency symptoms due to an error in the Hoagland solution. The plants died from nutritional toxicity befor the ten day photodynamic injury was evaluated.

Based on the photodynamic injury observed on day two, compositions containing ALA and modulators 488 and 814, respectively, were effective defoliants. Overall, the older mature leaves were more susceptible than the younger developing leaves, as was observed with tomato. Fifty seven of the modulators tested exhibited 90-100% defoliation of older leaves while twelve modulators exhibited similar performance on younger leaves. Seven of the modulators exhibited 100% defoliation of both young and old leaves.

These examples serve to demonstrate the novel concept of the present invention. The photodynamic mode of action is different from other known modes of action in two main respects: (a) it is dependent on the biosynthesis and accumulation of tetrapyrroles in the foliage of living plants; and (b) the accumulated tetrapyrroles render the foliage of the plants light-sensitive so that upon subsequent exposure to light, a very damaging photodynamic effect is produced which results in desiccation of the foliage without death of the plants.

δ-Aminolevulinic acid is a natural metabolite present in all living cells; it is a natural component of the biosphere and is readily biodegradable. The same is true for the products of ALA dark-metabolism, i.e., the tetrapyrrole intermediates of the Chl biosynthetic pathway, which have been demonstrated to disappear very rapidly upon exposure of the plant to light. Similarly, modulators which are naturally occurring vitamins or derivatives thereof, e.g., ethyl nicotinate, are expected to be readily biodegradable and to have no adverse impact on the environment. It therefore appears that the photodynamic desiccating compositions and methods of the present invention employing ALA and/or vitamins or derivatives thereof are likely to have no adverse impact on the environment.

Further examples of compositions and applications within the spirit and scope of this invention are described in copending application Ser. No. 895,529 and in Rebeiz, C. A. et al., *CRC Critical Reviews in Plant Sciences*, 6(4):385-436 (1988).

I claim:

1. A method for defoliating a deciduous tree comprising the steps of:
   (a) contacting said tree with a defoliating effective amount of δ-aminolevulinic acid; and
   (b) allowing said contacted tree of step (a) to be exposed to light.

2. A method as recited in claim 1, wherein said contacted tree of step (a) is exposed to a substantial absence of light at wavelengths of 300 to 700 mM before being exposed to light in step (b).

3. A method as recited in claim 1, wherein said contacted tree of step (a) is exposed to said substantial absence of light for about 1 to 8 hours before being exposed to light in step (b).

4. A method as recited in claim 1, wherein said tree is exposed to light in step (b) for a period of time sufficient to oxidize most unsaturated membrane lipoproteins of the foliage of said plant.

5. A method as recited in claim 1, wherein said tree is exposed to light in step (b) in the form of natural daylight for a period of about 1 to 14 days.

6. A method for causing defoliation and fruit drop in a deciduous fruit tree comprising the steps of:
   (a) contacting said tree with an amount effective to cause defoliation and fruit drop in said tree of δ-aminolevulinic acid; and
   (b) allowing said contacted tree of step (a) to be exposed to light.

7. A method as recited in claim 6, wherein said contacted tree of step (a) is exposed to a substantial absence of light at wavelengths of 300 to 700 mM before being exposed to light in step (b).

8. A method as recited in claim 6, wherein said contacted tree of step (a) is exposed to said substantial absence of light for about 1 to 8 hours before being exposed to light in step (b).

9. A method as recited in claim 6, wherein said tree is exposed to light in step (b) for a period of time sufficient to oxidize most unsaturated membrane lipoproteins of the foliage of said plant.

10. A method as recited in claim 6, wherein said tree is exposed to light in step (b) in the form of natural daylight for a period of about 1 to 14 days.

11. A method as recited in claim 1, wherein said effective amount of δ-aminolevulinic acid is at least 15 mM.

12. A method as recited in claim 6, wherein said effective amount of δ-aminolevulinic acid is at least 15 mM.

* * * * *